US007799116B2

(12) United States Patent
Schwindt

(10) Patent No.: US 7,799,116 B2
(45) Date of Patent: Sep. 21, 2010

(54) EVAPORATION VALVE

(76) Inventor: Jeffrey Schwindt, 6359 Brokenhurst Rd., Indianapolis, IN (US) 46220

( * ) Notice: Subject to any disclaimer, the term of this patent is extended or adjusted under 35 U.S.C. 154(b) by 249 days.

(21) Appl. No.: 11/970,168

(22) Filed: Jan. 7, 2008

(65) Prior Publication Data

US 2008/0161718 A1    Jul. 3, 2008

Related U.S. Application Data

(63) Continuation of application No. 10/420,296, filed on Apr. 22, 2003, now Pat. No. 7,316,726.

(51) Int. Cl.
*B01D 53/00* (2006.01)

(52) U.S. Cl. .......................... 95/39; 55/385.1; 55/466; 128/202.12

(58) Field of Classification Search .................. 95/39; 55/385.1, 466; 128/202.12; 600/566, 568
See application file for complete search history.

(56) References Cited

U.S. PATENT DOCUMENTS

| 5,873,256 A * | 2/1999 | Denniston ...................... 62/91 |
| 6,527,731 B2 * | 3/2003 | Weiss et al. ................... 600/566 |

* cited by examiner

*Primary Examiner*—Robert A Hopkins

(57) ABSTRACT

A pneumatic circuit and other components are provided for the operation of a medical device. The pneumatic circuit provides controlled pressurized air to a medical device for use during a medical procedure.

20 Claims, 36 Drawing Sheets

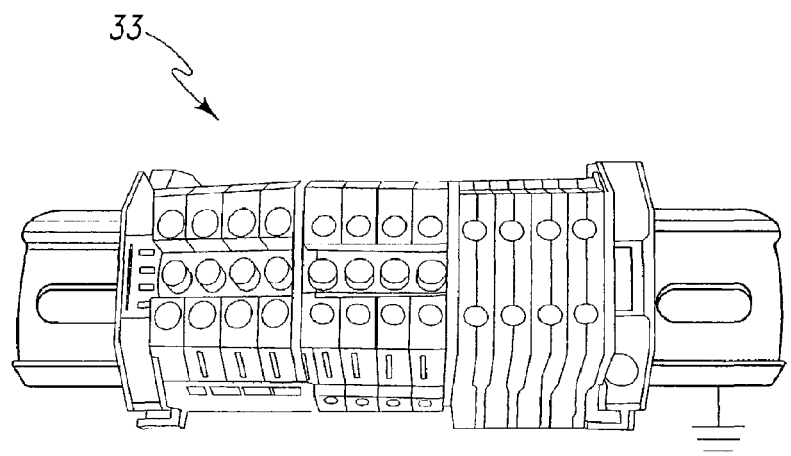
Fig. 14
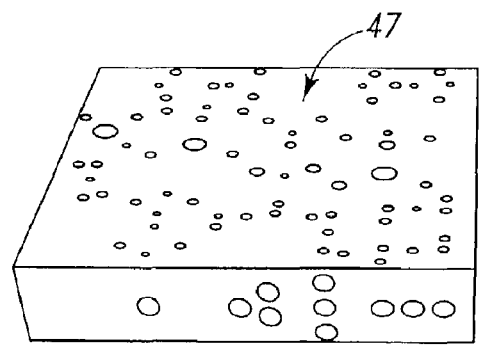 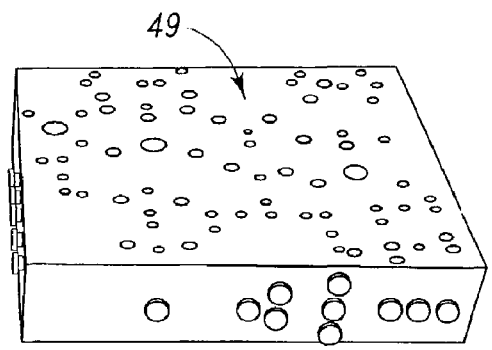
Fig. 15A          Fig. 15B

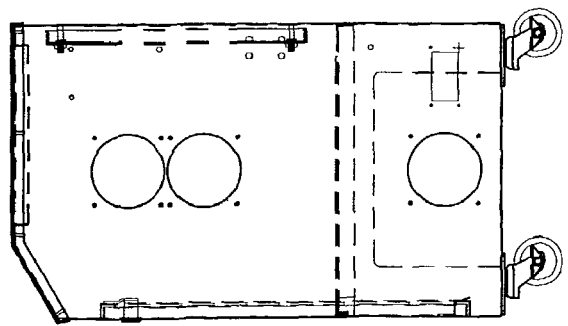
Fig. 19D
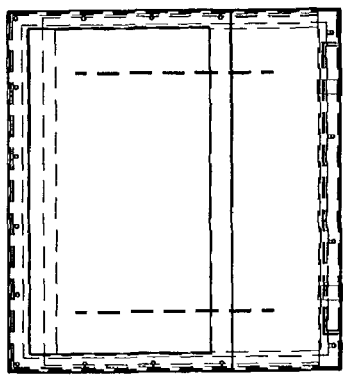
Fig. 19B
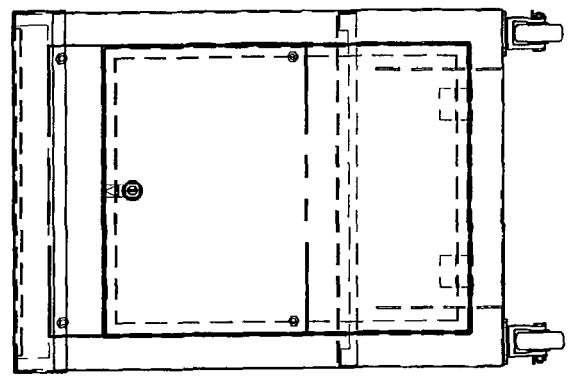
Fig. 19C
Fig. 19A

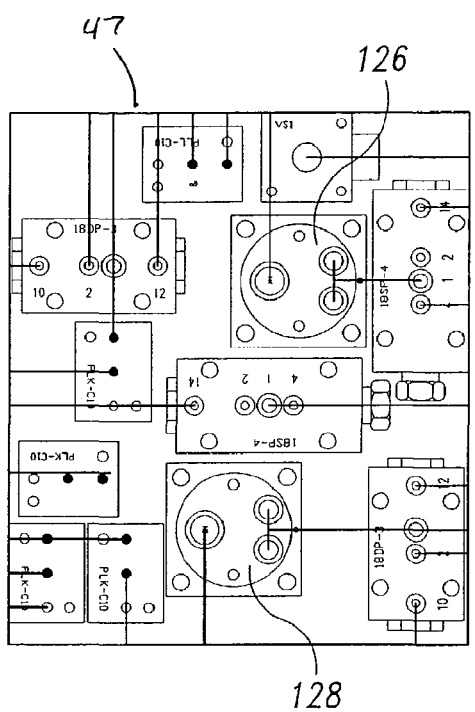
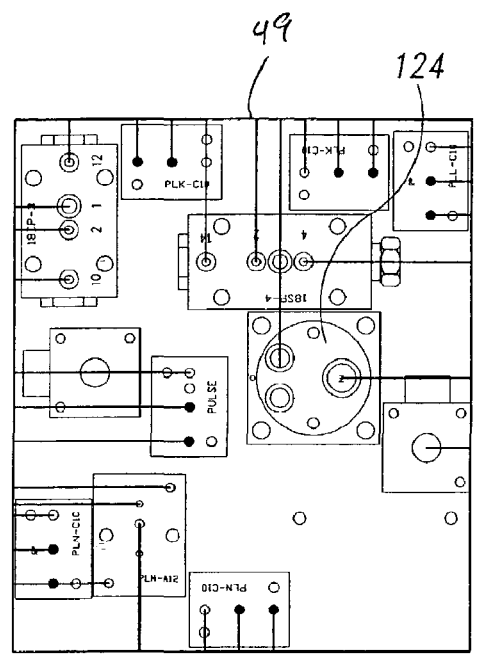
Fig. 21A    Fig. 21B
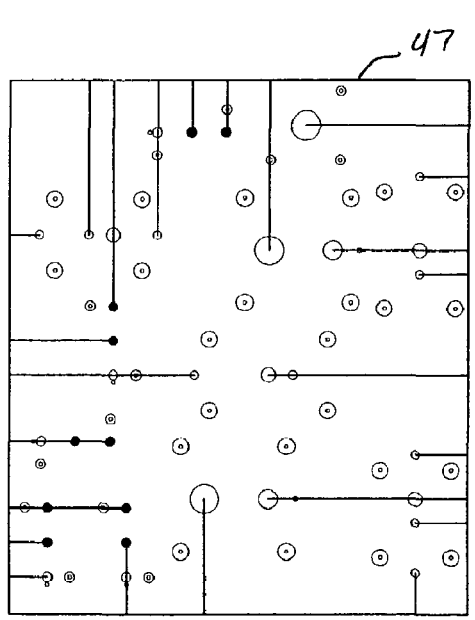
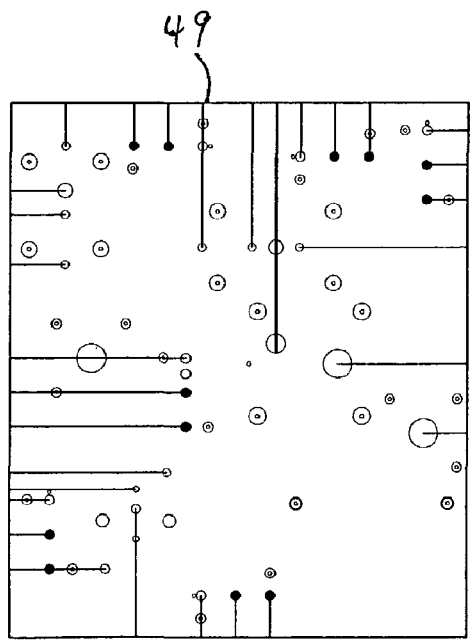
Fig. 21C    Fig. 21D

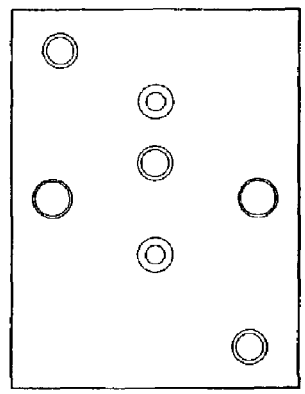
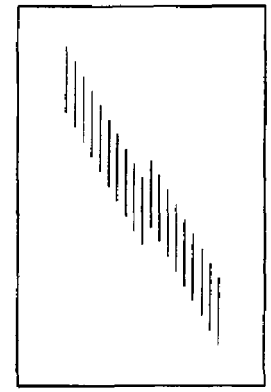
Fig. 23A        Fig. 23B
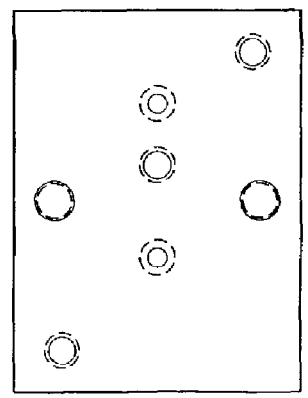
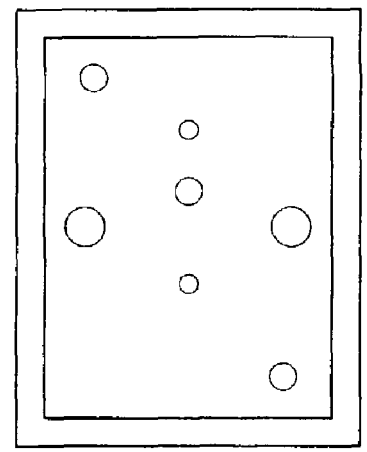
Fig. 23C        Fig. 23D

Fig. 34A

Kit List  
Date: 03/23/02  
Page No: 1

ASE-1420-C CONTROL SYSTEM

| Part Name-# | Description | Quantity |
|---|---|---|
| fvs-361 | F-A FVS-361 SPECIAL 18SP-4 | 3 |
| fvs-362 | F-A FVS-362 SPECIAL 18DP-3 | 3 |
| nv-55 | FABCO NV-55 NEEDLE VALVE | 2 |
| 1020 | F-A 1020 COUPLER | 2 |
| mcd-1204 | CPC MCD-1204 COUPLER | 2 |
| zb2-bd2 | T-E ZB2-BD2 BLK SELECTR SWITC | 2 |
| zb2-bz009 | T-E ZB2-BZ009 MTG. RING | 2 |
| pxb-b1911 | T-E PXB-B1911 CONTACT BLOCK | 3 |
| pxb-b1921 | T-E PXB-1921 NP CONTACK BLK | 2 |
| pxv-m131 | T-E PXV-M131 GREEN INDICATOR | 1 |
| plm-a10 | T-E PLM-A10 MEMORY RELAY | 1 |
| pll-c10 | T-E PLL-C10 "AND" GATE | 1 |
| pln-c10 | T-E PLN-C10 NOT RELAY | 1 |
| plk-c10 | T-E PLK-C10 "OR" GATE | 6 |
| lfpul10/0.5 | T-E LFPUL10/0.5 PULSE VALVE | 1 |
| plk-a11 | T-E PLK-A11 "OR" ELEMENT | 1 |
| f-4200-60-mm | A-T F-4200-6-MM PRESSURE SWITCH | 1 |
| vp-701-30-mm | A-T VP-701-30-MM SWITCH | 1 |
| pp-701-30-mm | A-T PP-701-30-MM SWITCH | 1 |
| f-05-062 | A-T F-05-062 FILTER | 1 |
| k2-202e-n | RECTUS K2-202E-N COUPLER | 2 |
| k2-2027e-n | RECTUS K2-2072E-N COUPLER | 2 |
| n3-202e-m-n | RECTUS N3-202E-M-N PLUG | 2 |
| 20sfaw10mxns | RECTUS 20SFAW10MXNS | 2 |
| 88050-04 | ALPHA 88050-04 BULKHEAD CON. | 1 |
| 88800-53 | ALPHA 88800-53 CARTRIDGE | 38 |
| 88800-04 | ALPHA 88800-04 CARTRIDGE | 8 |
| 88000-53-02 | ALPHA 88000-53-02 STRT.ML.CON. | 1 |
| 88115-53-32 | ALPHA 88115-53-32 ML.SVL.ELBW. | 6 |
| 88110-04-02 | ALPHA 88110-04-02 ML.SVL.ELBW. | 2 |
| 88215-53-32 | ALPHA 8215-53-32 SWV BRCH TEE | 5 |
| 88700-04-53 | ALPHA 88700-04-53 REDUCER | 6 |
| 88310-53 | ALPHA 88310-53 UNION Y | 10 |
| 88310-04 | ALPHA 88310-04 UNION Y | 2 |
| 88230-53 | ALPHA 88230-53 UNION TEE | 3 |
| 88230-04 | ALPHA 88230-04 UNION TEE | 5 |
| 88040-04 | ALPHA 88040-04 UNION CON. | 2 |
| 88020-53-32 | ALPHA 88020-53-32 STRT.ML.CON. | 2 |
| al9840 | F-W AL9840 SPECIAL ASSEMBLY | 15 |
| bm-18 | ADSEN BM-18 MUFFLER | 7 |
| bm-08 | ADSEN BM-08 MUFFLER | 2 |
| .75-arsr-1.0 | L-A .75-ARSR-1.0 CYLINDER | 1 |

(Continued on following page)

Fig. 34B

Kit List

Date: 03/23/02
Page No: 2

ASE-1420-C CONTROL SYSTEM

| Part Name-# | Description | Quantity |
|---|---|---|
| ro1-12a-k | M-I R01-12A-K REGULATOR | 2 |
| ro1-10a-k | M-I R01-10A-K REGULATOR | 1 |
| 11708 | M-I 11708 ADAPTER | 3 |
| 204-2209-2 | M-I 204-2209-2 FILTER | 1 |
| 104-3101-2 | M-I 104-3101-2 RELIEF REG. | 1 |
| cds-4p-004d | D-F CDS-4P-004D GAUGE | 2 |
| cds-4p-010d | D-F CDS-4P-010D GAUGE | 2 |
| 122a-2x2 | ALKON 122A-2X2 1/8" HEX NIPPLE | 3 |
| 100a-2 | ALKON 100A-2 1/8" UNION ELBOW | 3 |
| plj-1/4" | PISCO PLJ-1/4" ELBOW | 3 |
| mcv-1 | CLIPPARD MCV-1 VALVE | 2 |
| 5a708 | GRAINGER 5A708 RELIEF VALVE | 1 |
| al445 | GAST AL445 MUFFLER | 1 |
| 0353-6-6 | PARKER 0353-6-6 BULKHEAD | 1 |
| 0253-4-6 | PARKER 0253-4-6 BULKHEAD | 1 |
| 2303-6-6 | PARKER 2303-6-6 ELBOW | 1 |
| 2103-4-6 | PARKER 2103-4-6 ELBOW | 2 |
| 2203-4-6 | PARKER 2203-4-6 ELBOW | 1 |
| 919-0639-6-6-6 | PARKER 919-0639-6-6-6-10" | 1 |
| 919-0606-6-6-6 | PARKER 919-0606-6-6-6-14" | 1 |
| 919-0606-6-6-6- | PARKER 919-0606-6-6-6-19" | 1 |
| 3p-30a2-s | L-M 3P-30A2-S FOOT SWITCH | 1 |
| g.75x2whg | PANDUIT G. 75X2WHG DUCT | 5 |
| c.75whg | PANDUIT C. 75WHG COVER | 5 |
| cc072x38x1s | L-S CC072X38X1S SPRING | 8 |
| 5692t24 | M-C 5692T24 FOAM | 4 |
| 91843a118 | M-C 91843A118 ROUND NUT | 1 |
| 93505a850-6/32 | M-C 93505A850-6/32 STAND OFF | 2 |
| 6120g1an | LYTRON 6120G1AN HEAT EXCHANGER | 1 |
| 11845a11 | M-C 11845A11 HOOK | 1 |
| 81f8103 | NEWARK 81F8103 FAN | 5 |
| 81f2738 | N-W 81F2738 GUARD | 5 |
| 81f2747 | N-W 81F2747 POWER CORD | 5 |
| 64f276 | N-W 64F276 SIGNAL | 1 |
| 16f9371 | N-E 16F9371 10 AMP FILTER | 1 |
| a2207-11 | AIC A2207-11 ENTRY MODULE | 1 |
| 800em-lfa3 | A-B 800EM-LFA3 OPERATOR | 1 |
| 800e-2dl5g | A-B 800E-2DL5G MODULE | 1 |
| 800e-2x10 | A-B 800E-2X10 CONTACT | 2 |
| 3p | H-P 3P AIR VALVE | 1 |
| 3822-03-5287 | SPARTAN 3822-03-5287 VALVE | 2 |
| ase-1420-c | ASE-1420-C CONTROL SYSTEM | 1 |

ASE-1420 PARTS SUPPLIERS

| MANUFACTURER | ABBREVIATION | CITY, STATE | PARTS PROVIDED |
|---|---|---|---|
| FABCO-AIR | F-A | GAINESVILLE, FL | 3&4 WAY VALVES, NEEDLE VALVES |
| COLDER PRODUCTS | CPC | ST. PAUL, MN | HANDPIECE QUICK DISCONNECTS |
| TELEPNEUMATIC/PARKER | T-E | RICHLAND, MI | LOGIC COMPONENTS & FOOT SWITCH |
| AIRTROL | A-T | NEW BERLING, WI | PRESSURE & VACUUM SWITCHES |
| RECTUS/TEMA | RECTUS | SPARTA, NJ | FT SWITCH QUICK DISCONNECTS |
| ALPHA TECHNOLOGIES | ALPHA | FRANKLIN, TN | FITTINGS |
| FREELIN-WADE | F-W | MCMINNVILLE, OR | TUBING |
| ADSENS | ADSEN | CITY OF INDUSTRY, CA | MUFFLERS |
| LIN-ACT/PARKER | L-A | DES PLAINES, IL | VOLUME CHAMBER |
| MONNIER | M-I | ALGONAC, MI | REGULATORS AND FILTERS |
| DYNAMIC FLUID COMPONENTS | D-F | WEST UNION, SC | GAUGES |
| ALKON CORPORATION | ALKON | CHICAGO, IL | BRASS FITTINGS |
| CLIPPARD | CLIPPARD | CINCINNATI, OH | CHECK VALVES |
| GRAINGER | GRAINGER | INDIANAPOLIS, IN | RELIEF VALVE |
| GAST MFG | GAST | BENTON HARBOR, MI | PUMPS |
| PARKER FITTINGS | PARKER | WICKLIFFE, OH | HIGH TEMP HOSES |
| PANDUIT | PANDUIT | TINLEY PARK, OH | WIRE DUCT |
| LEE SPRING | L-S | BROOKLYN, NY | MOTOR MOUNTS |
| MCMASTER-CARR | M-C | CHICAGO, IL | ACOUSTICAL FOAM |
| LYTRON | LYTRON | BOSTON, MA | HEAT EXCHANGER |
| NEWARK ELECTRONICS | N-W | PALATINE, IL | FANS, BREAKER, POWER ENTRY, FILTER |
| ALLEN-BRADLEY/ROCKWELL | A-B | MILWAUKEE, WI | TERMINALS, ON/OFF SWITCH |
| SPARTAN SCIENTIFIC | SPARTAN | BOARDMAN, OH | DUMP VALVES |
| HUMPHREY PRODUCTS | H-P | KALAMAZOO, MI | TEST BUTTON VALVE |
| STANDARD CHANGE MAKERS | SCM | INDIANAPOLIS, IN | CABINET |
| JWS MACHINE | JWS | BRAZIL, IN | MANIFOLDS AND OTHER MACHINED PARTS |

Fig. 34C

EVAPORATION VALVE

CROSS-REFERENCE TO RELATED APPLICATIONS

This application claims the benefit of U.S. Ser. No. 10/420,296 filed Apr. 22, 2003, which claims the benefit of U.S. Ser. No. 60/374,952 filed Apr. 23, 2002.

BACKGROUND OF INVENTION

The present invention relates to a pneumatic circuit, and particularly to a pneumatic circuit for use in the operation of an at least partially air-powered tool. More particularly, the present invention relates to a pneumatic circuit useful in the pneumatic operation of a medical device.

SUMMARY OF INVENTION

The present disclosure relates to one or more of the following features, elements or combinations thereof. A pneumatic control system is provided for use with a medical device, illustratively a suction biopsy device. The suction biopsy device has a cannula for insertion into a body to a point adjacent to a mass to be examined, and a rotating cutter device is housed within.

A rinse or illustratively saline solution is provided for assisting in the removal of the mass to be examined. A suction is provided for assisting in the removal of the mass to be examined. The control system has an absence of electrical circuitry configured to control the operation of the suction biopsy device. Electrical power is illustratively provided only for the compressor and the vacuum.

A pinch valve is provided. The pinch valve is configured to provide for non-slip line attachment. The pinch valve has a central catch and two opposing catches. A piston is positioned to cooperate with the central catch to reduce the flow of fluid through the line. The piston is controlled pneumatically.

The control system includes a water evaporation assembly. The water evaporation assembly includes a filter, a relief regulator, and a permeable exhaust member. The permeable exhaust member is positioned to point upwardly, dissipating moisture from the control system into the environment. The permeable exhaust member causes the dissipated moisture to evaporate as it is dissipated.

The control system comprises a pressurized gas conduit coupled to a compressor, the conduit having an exit port. A gas-permeable absorber is coupled to the exit port, wherein the absorber is used to collect moisture in the pneumatic circuit and dissipate the moisture into the atmosphere through the absorber. The pressurized gas is used to actuate the medical device.

A vacuum system is configured to create a vacuum in the circuit. The absorber comprises an intake filter not normally configured for use as an absorber, but which absorbs moisture when the pressurized gas is directed through it. A cabinet is provided for housing substantially all of the pneumatic circuit, and the absorber is positioned within the cabinet.

Liquid condensed in the pneumatic circuit is illustratively not collected in a liquid reservoir for collecting the condensed liquid.

The biopsy device is composed substantially of polymeric materials and non-magnetic metals and can be used in conjunction with a Magnetic Resonance Imaging device. The absorber comprises a pneumatic filter typically used for filtering intake gases.

A method of removing moisture from a compressed gas system housed in a cabinet is also provided. The method comprises the steps of compressing the gas with a compressor, directing the compressed gas through a conduit to an exit port, directing the compressed gas through the exit port and through a gas-permeable absorber connected to the exit port, and using the absorber to collect moisture from the compressed gas and dissipate the moisture into the atmosphere inside the cabinet.

The absorber is mounted such that it extends from the exit port in a substantially vertically upward direction. The conduit comprises at least one of a heat exchanger, a coalescing filter, and a tube.

In another embodiment, a method of providing compressed gas to a medical device comprises the steps of compressing the gas with a compressor, directing the compressed gas through a conduit to a liquid absorber, directing the compressed gas through the absorber, and using the absorber to collect moisture from the compressed gas and dissipate the collected moisture into the atmosphere.

Additional features of the disclosure will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 14 is a view of the terminal block subassembly;

FIGS. 15A-B are perspective views of the two manifolds configured to route the pneumatic tubing within the console;

FIGS. 19A-D show specification drawings for the console;

FIGS. 21A-D show diagrammatic representations of the manifolds depicting the ports and internal passageways associated with the manifolds;

FIGS. 23A-D show specification drawings for the gasket;

FIGS. 34A-C show parts listings of the various parts used in the construction of the Breast Biopsy System.

DETAILED DESCRIPTION OF THE DRAWINGS

Figure 1:
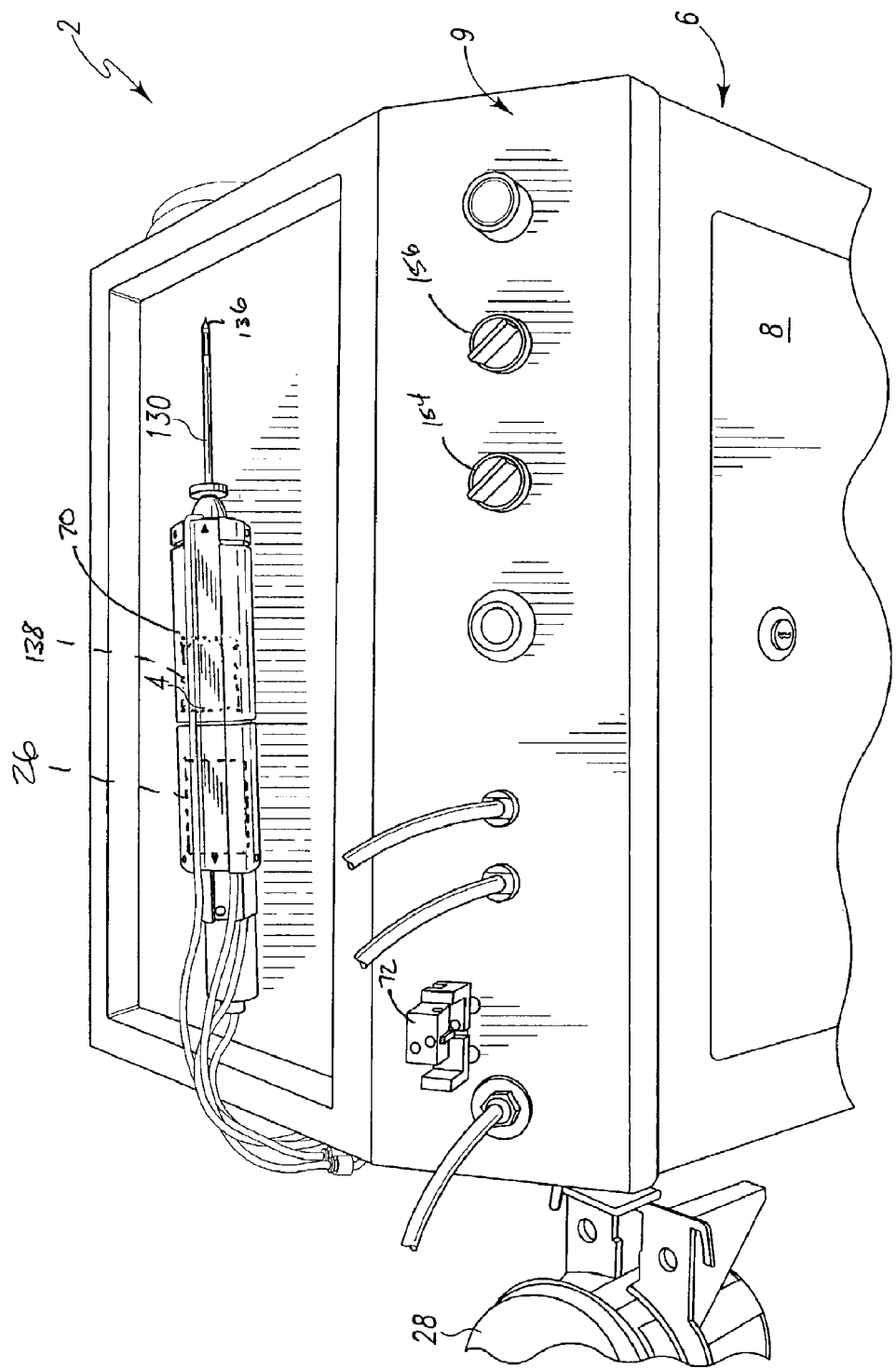
FIG. 1 is a top perspective partial view of a Breast Biopsy System having a hand wand, the Biopsy System including a pneumatic circuit internally, the circuit configured to operate the Biopsy System and hand wand.
Figure 2:
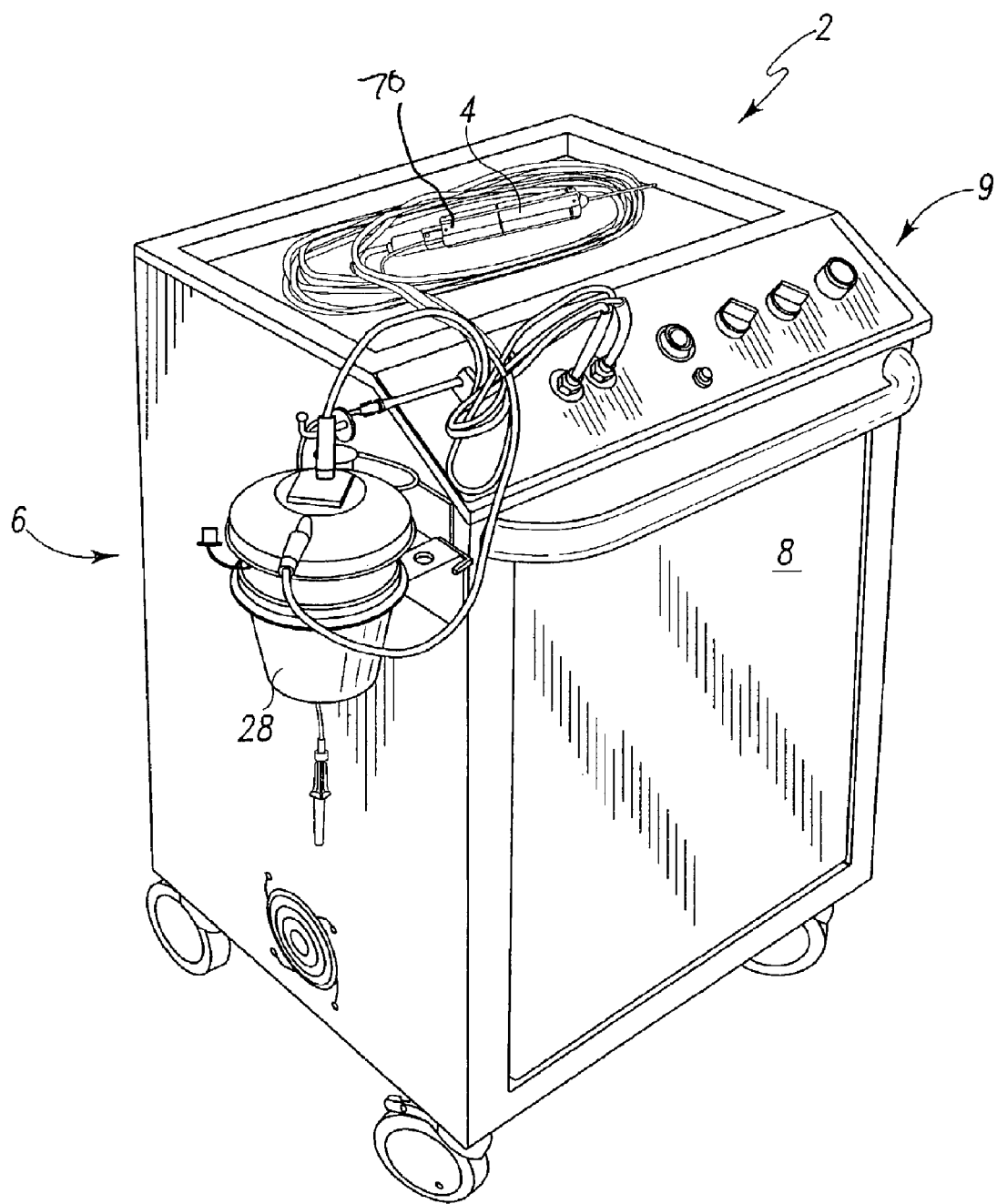
FIG. 2 is a perspective view of the system shown in FIG. 1.
Figure 17:
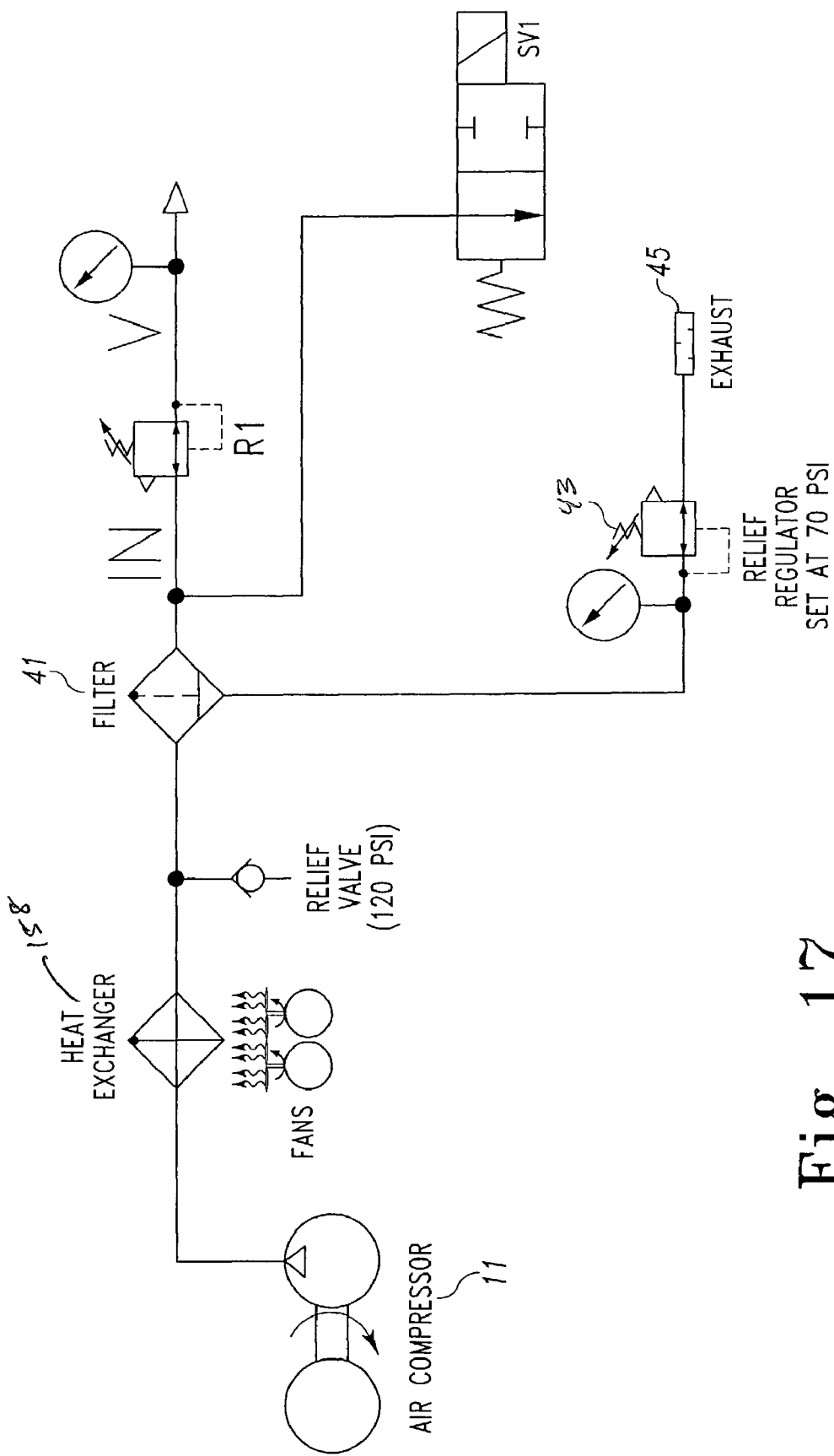
FIG. 17 is a schematic representation of an evaporation valve portion of the pneumatic circuit.
Figure 18:
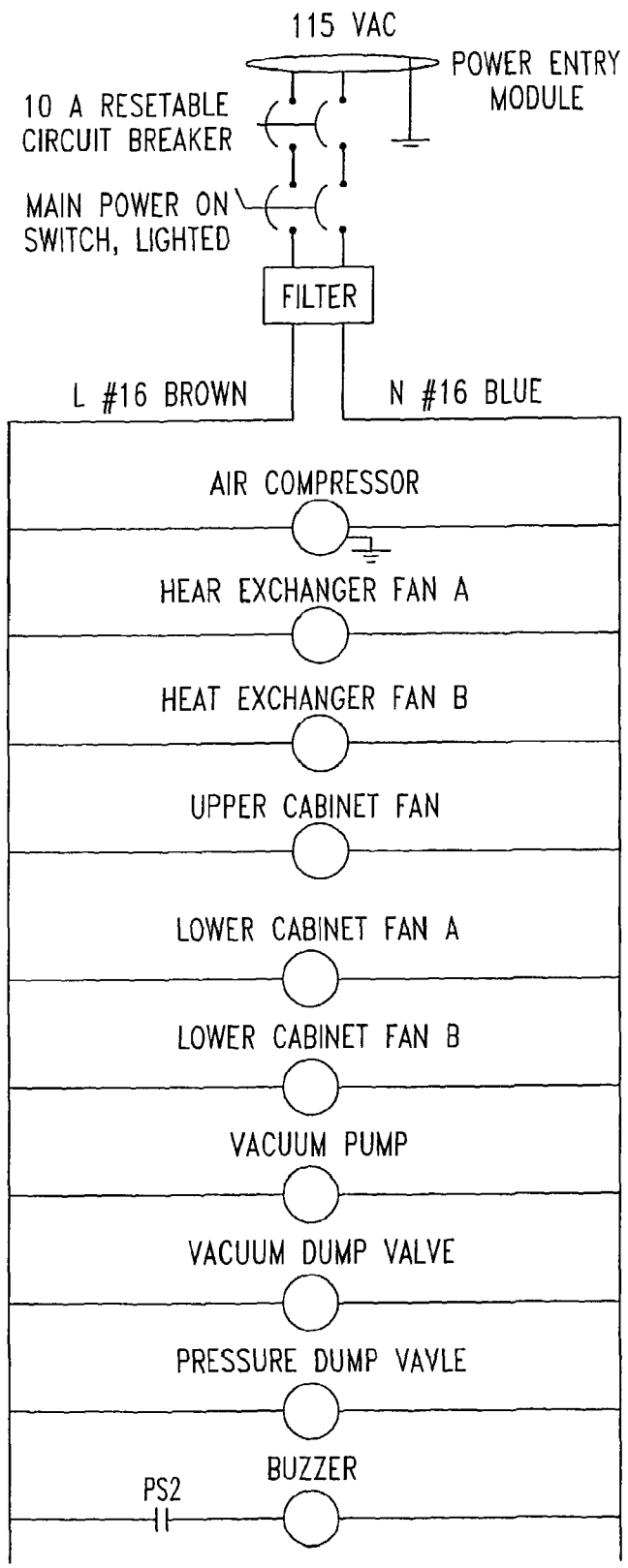
FIG. 18 is another schematic representation of a portion of the pneumatic circuit.
Figure 20A:
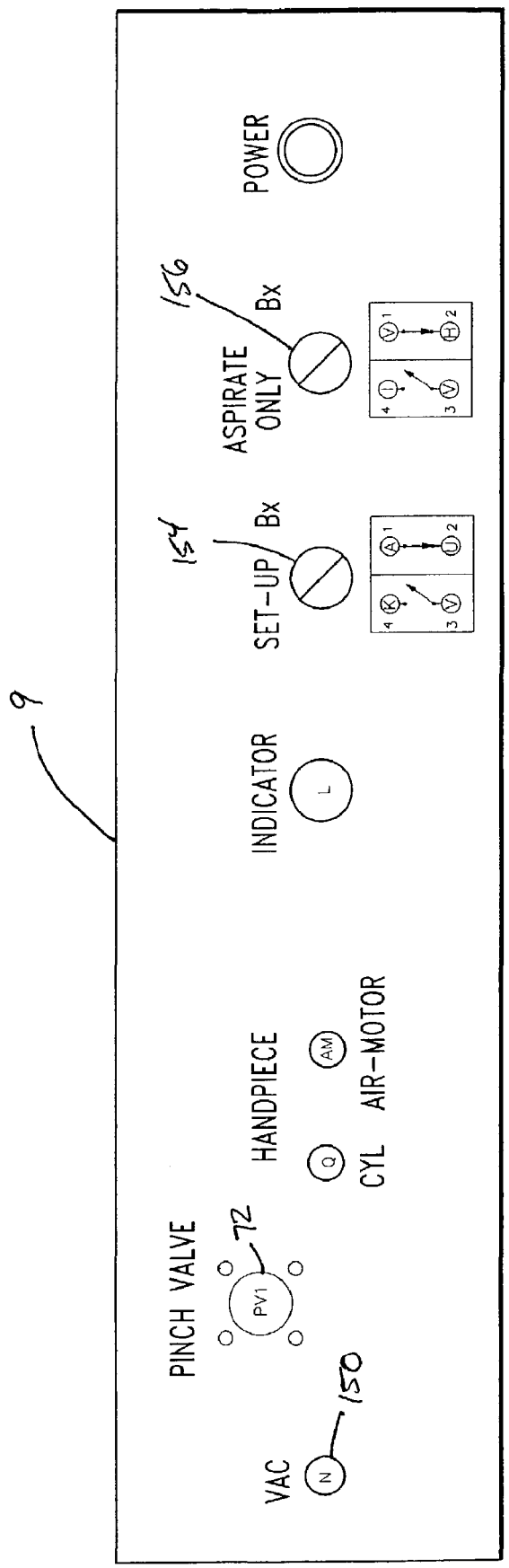
FIG. 20A shows the configuration of the control panel.
Figure 20B:
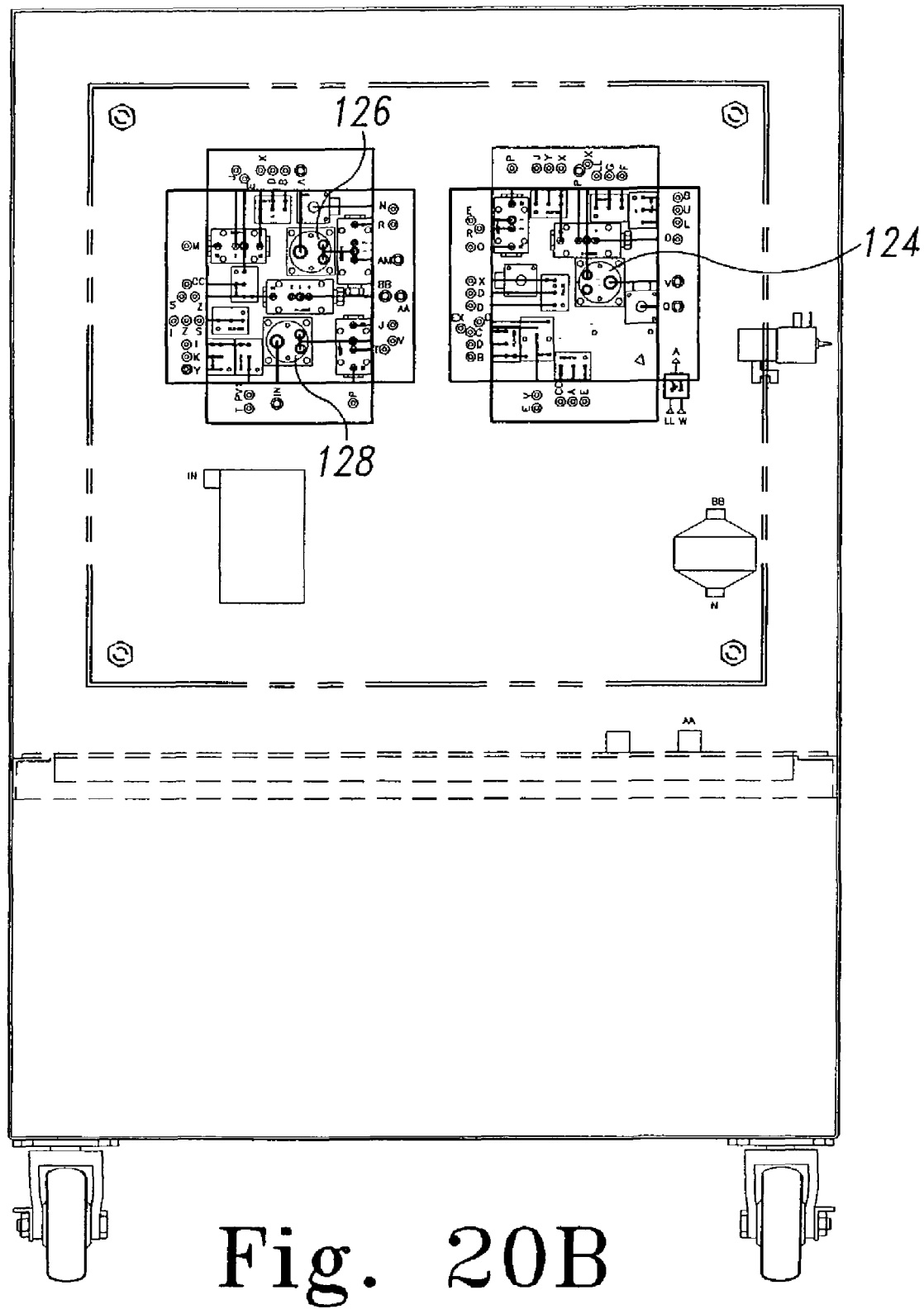
FIG. 20B shows the configuration of the manifolds with relation to the filters and connection points.

One embodiment of the present disclosure is shown in FIGS. 1 and 2 in the form of a Breast Biopsy System 2 having a hand wand 4. Biopsy System 2 illustratively includes a console 6 having an access door 8 and a control panel 9 positioned toward the top of the console 6. Biopsy System 2 includes an internal pneumatic circuit 10 (shown in FIGS. 8-12 and schematically in FIGS. 16-18) that is configured to operate a medical device 70, illustratively hand wand 4, as will be discussed in more detail below. It should be understood that as used herein, medical device 70 can be any medical device that is powered at least in part by pneumatic pressure. The illustrative medical device 70 comprises a hand wand 4, and such terms are used interchangeably throughout.

Figure 3A:
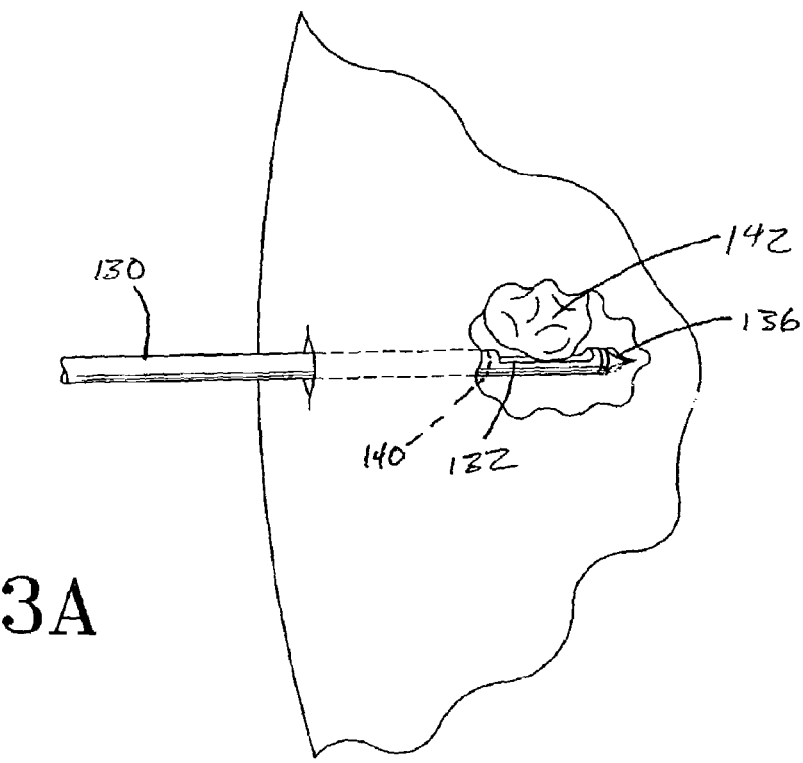
FIG. 3A is a view of the cannula of the hand wand inserted into a patient's breast adjacent a tissue mass, the cannula having an aperture positioned adjacent the mass.
Figure 3B:
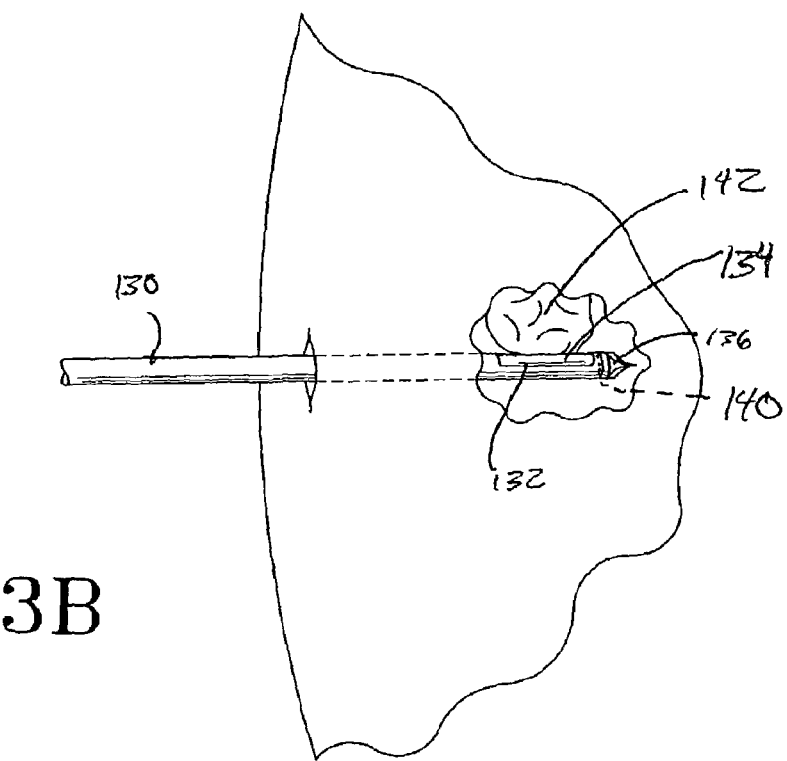
FIG. 3B is a view similar to that of FIG. 3A, showing a cylindrical cutter that has moved inside the cannula, thereby cutting away a portion of the tissue mass.

Biopsy System 2, and particularly hand wand 4, illustratively function in the following manner. A patient having a mass 142 to be removed receives a local anesthetic and the mass is identified and located in the patient. Location methods may include ultrasound, magnetic resonance imaging (MRI), X-Ray, or any other method known in the medical industry. As can be seen in FIGS. 1 and 3A-B, hand wand 4 illustratively includes a hollowed needle or cannula 130 extending therefrom, the cannula 130 having a sharp distal end 136 for facilitating piercing into the patient's body, and the cannula 130 further having a cutter 134 positioned therein for rotational and axial movement relative to the cannula 130. Cutter 134 is illustratively a cylindrical blade, but other configurations are within the scope of the disclosure. Distal end 136 is illustratively a frusto-conical stainless steel tip press-fitted on the end of cannula 130, the tip having a plastic cutting board (not shown) housed within for receiving cutter 134 when cutter 134 is at its full stroke position.

An aperture 132 is illustratively formed in the cylindrical wall of cannula 130 at its distal end. During operation, as shown in FIGS. 3A-B, a physician inserts cannula 130 into the patient (i.e. the cannula is inserted into a woman's breast) such that aperture 132 is positioned proximal to a mass 142 to be removed. While the cannula is being inserted into the patient's body, the cylindrical cutter 134 is positioned inside cannula 130 such that cutter 134 substantially closes off aperture 132. Pneumatic circuit 10 directs compressed air to pneumatic cylinder 26 in order to position cutter 134 at its full stroke position.

After cannula 130 is in position in the patient's body, pneumatic circuit 10 directs the retracting and advancing movement of cutter 134 relative to the cannula 130 in response to signals from a foot switch 16, a remote push button 18, or a panel push button 18A (see FIG. 16B) operated by a medical technician or surgeon. Once the operator signals for the cutting to begin, pneumatic circuit 10 directs vacuum pressure to hand wand 4, and pneumatic circuit releases the compressed air from pneumatic cylinder 26 (which is illustratively housed in hand wand 4). Once compressed air is released from pneumatic cylinder 26, a spring urges the plunger in pneumatic cylinder 26 toward the retracted position, thereby causing cutter 134 to move to the retracted position, consequently opening aperture 132. Vacuum pressure is also applied by pneumatic circuit 10 to the inside of cannula 130, causing a portion of the mass 142 to be drawn inside cannula 130. While the portion of the mass 142 is drawn inside cannula 130, pneumatic circuit 10 sends compressed air to cylinder 26, thereby moving cutter 134 relative to aperture 132 toward the extended, full-stroke position. At substantially the same time, pneumatic circuit 10 further directs compressed air toward a pneumatic motor 138 housed in hand wand 4. Pneumatic motor 138 is coupled to cutter 134 and causes cutter 134 to rotate about its axis inside cannula 130. As a result of the rotational and axial movement of cannula 130, cutter 134 cuts the portion of the mass 142 that extends inside the cannula 130 as cutter moves toward distal end 136 of cannula 130.

Once cutter 134 has completed such a cycle and has returned to the position wherein aperture 132 is closed, pneumatic circuit 10 confirms whether further cutting is necessary. Such confirmation is received from foot switch 16 or remote push button 18/panel push button 18A, described further herein. In the illustrated embodiment, a short pause of approximately a half second prior to confirmation allows sufficient time for an operator to determine whether additional cutting will be necessary.

If additional cutting is not deemed to be required and the mass 142 is considered removed, the operator removes cannula 130 from the patient's body. If instead confirmation is made that additional cutting is required, pneumatic cylinder 26 causes cutter 134 to again move to the retracted position, thereby opening the aperture 132, and saline is directed through the hand wand 4 and between cannula 130 and cutter 134. Saline passing over the cutting end 140 of cutter 134 is suctioned into the central portion of the cannula 130 with urging from the aforementioned applied vacuum pressure. Suctioning saline through the central portion of cannula 130 serves to flush the cut portion of the mass through the cannula toward a waste canister 28, described further herein. Additionally, the saline serves as a lubricant between the cannula 130 and the cutter 134. In the illustrative embodiment, pneumatic motor 138 is not actuated while cutter 134 is moved toward the retracted position, therefore cutter 134 does not rotate relative to cannula 130 during this retraction phase. Such operation is desirable so that tissue does not wrap around cutter 134 as cutter 134 retracts.

Pneumatic circuit 10 directs the continuous above-described cycling of cutter 134 as long as foot switch 16 or remote push button 18 or panel push button 18A is depressed. Illustratively, ultrasound, magnetic resonance imaging (MRI), or other mass-locating methods known in the art may be used during the procedure in order to monitor the progress of the removal of the mass 142. It is advantageous that Breast Biopsy System 2, in one embodiment, can be used in conjunction with an MRI device because of the majority of its components being pneumatic and non-magnetic.

Figure 4:
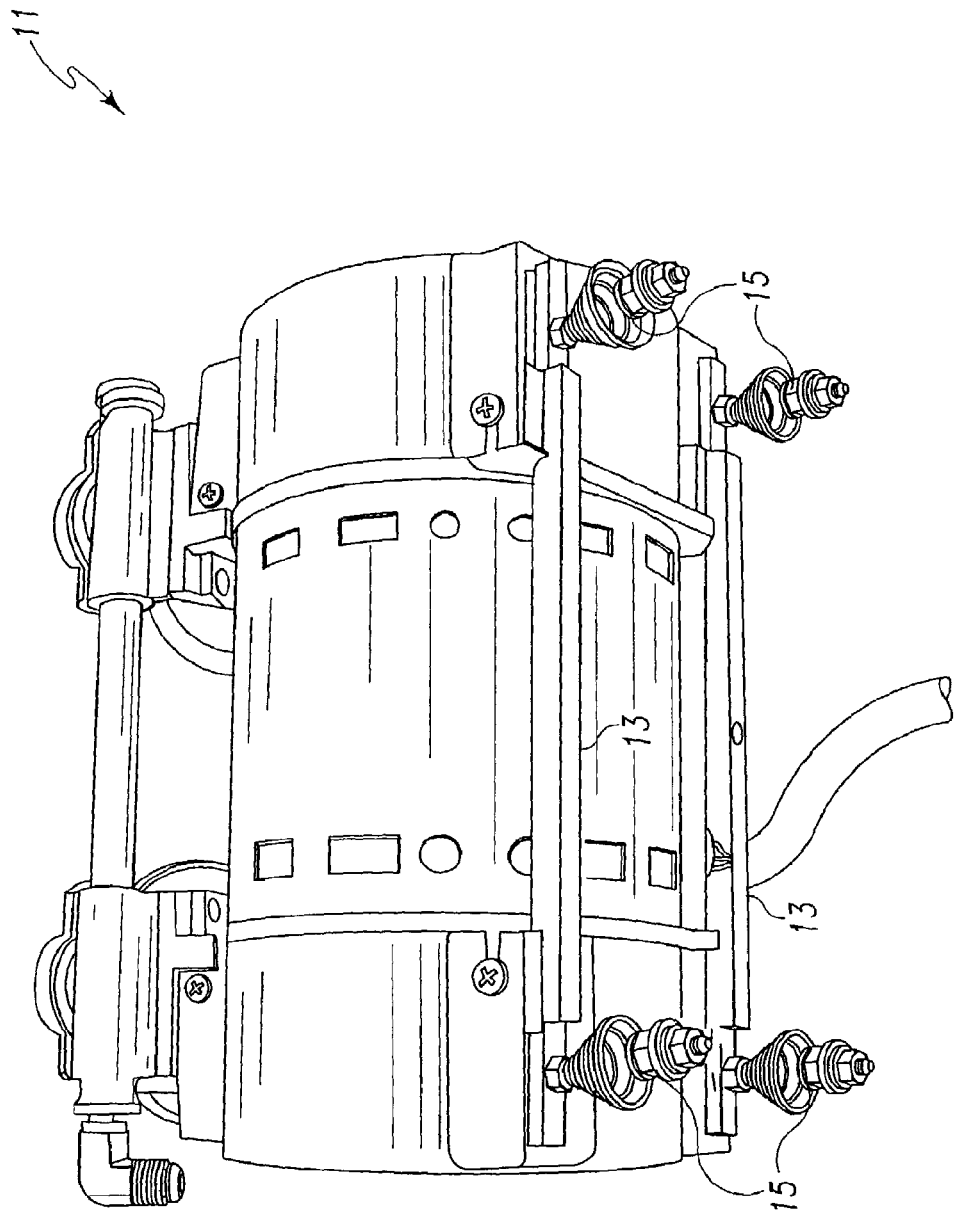
FIG. 4 is a view of an air compressor shown upside down with tie-down rails and springs attached.
Figure 5:
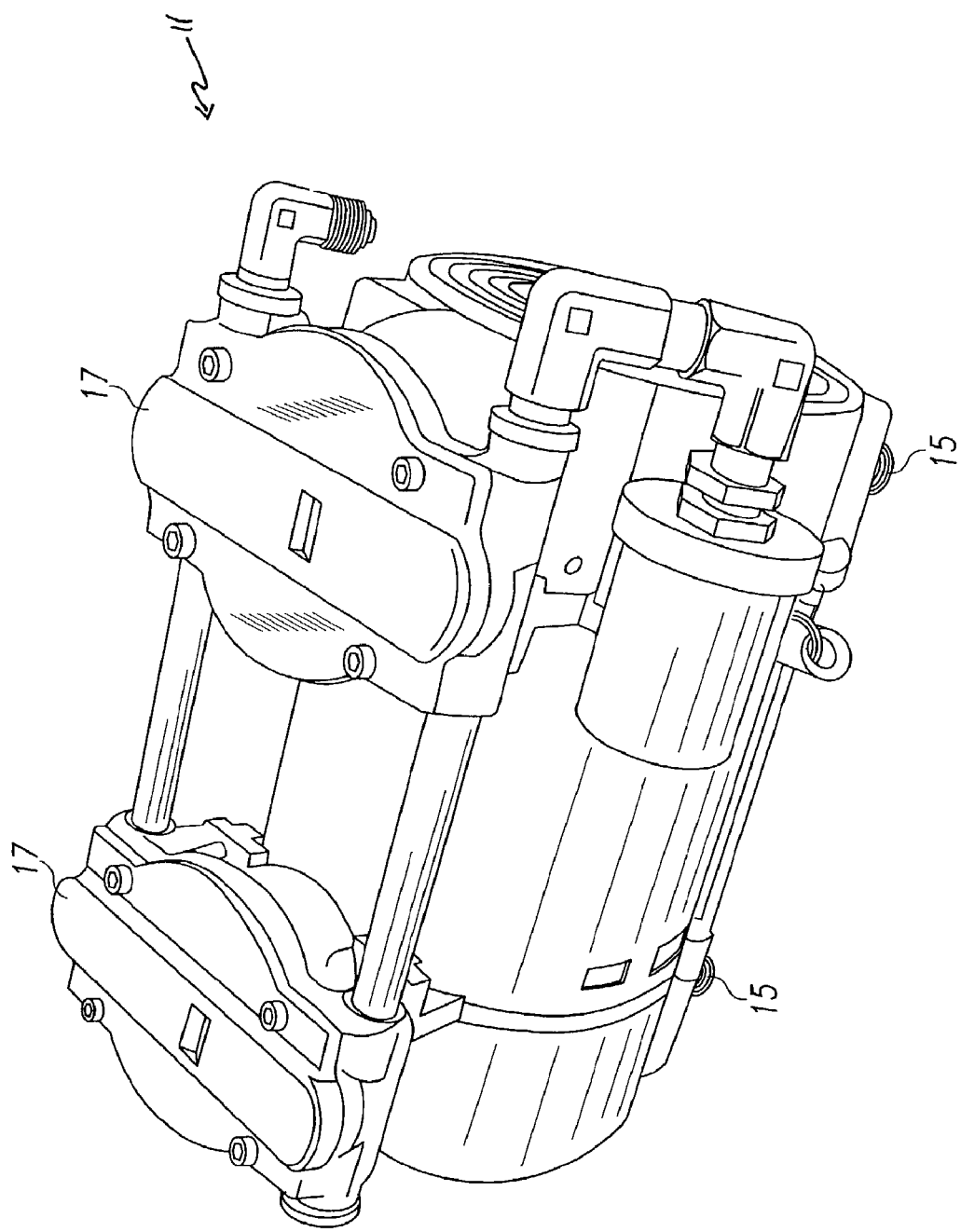
FIG. 5 is a view of the compressor of FIG. 4, showing the compressor right side up with additional fittings.
Figure 7:
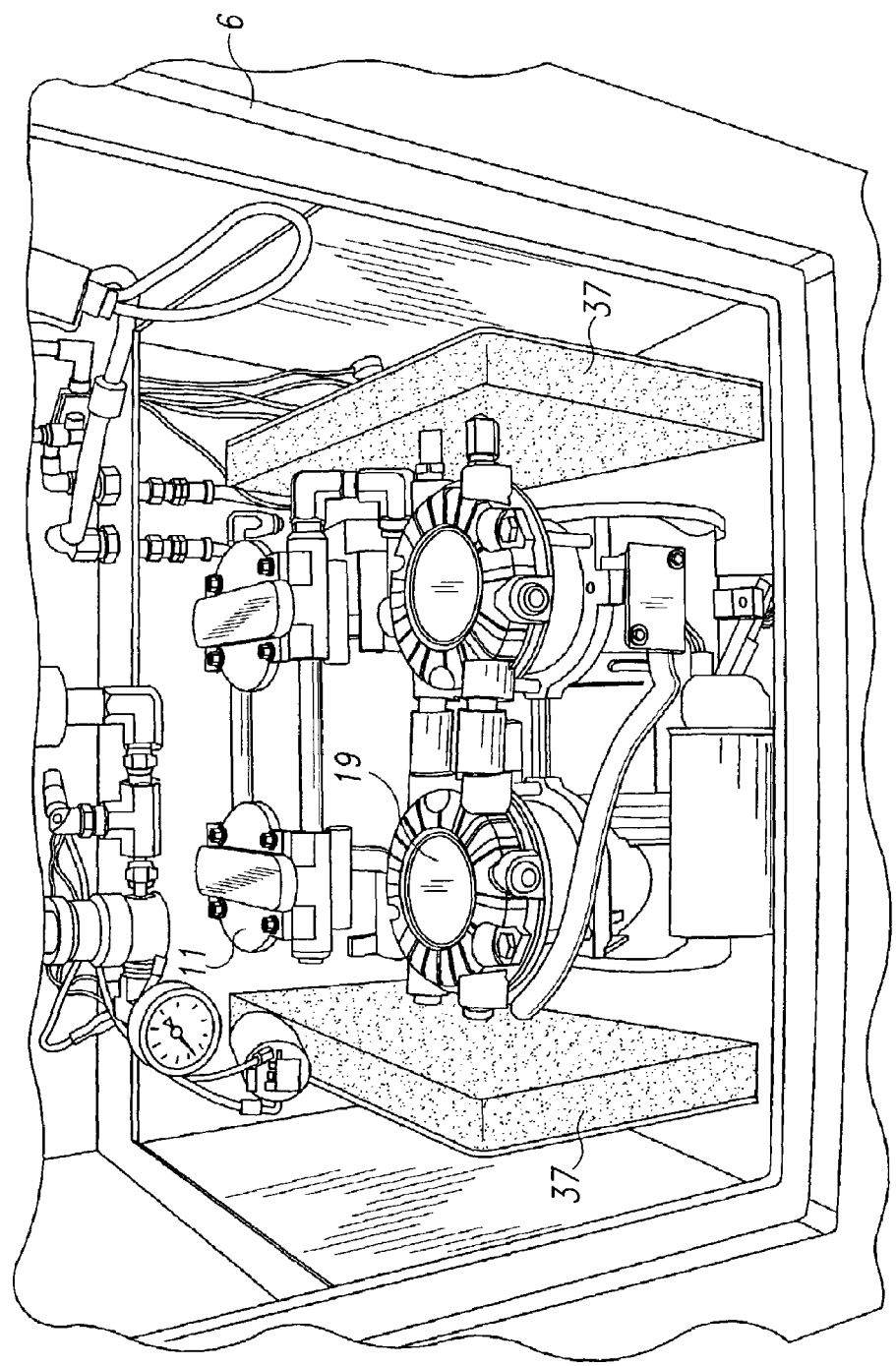
FIG. 7 is a view of the compressor of FIGS. 4-5 and the vacuum pump of FIG. 6 both installed in a console.

The components comprising pneumatic circuit 10, and their associated functions in the control of hand wand 4, are described below. FIGS. 4 and 5 show views of an air compressor 11 having tie-down rails 13 and springs 15 attached thereto. Fittings 17 are coupled to the top of air compressor 11 as shown in FIG. 5, and air compressor 11 is illustratively mounted in the rear of the console 6 as shown in FIG. 7.

Figure 6:
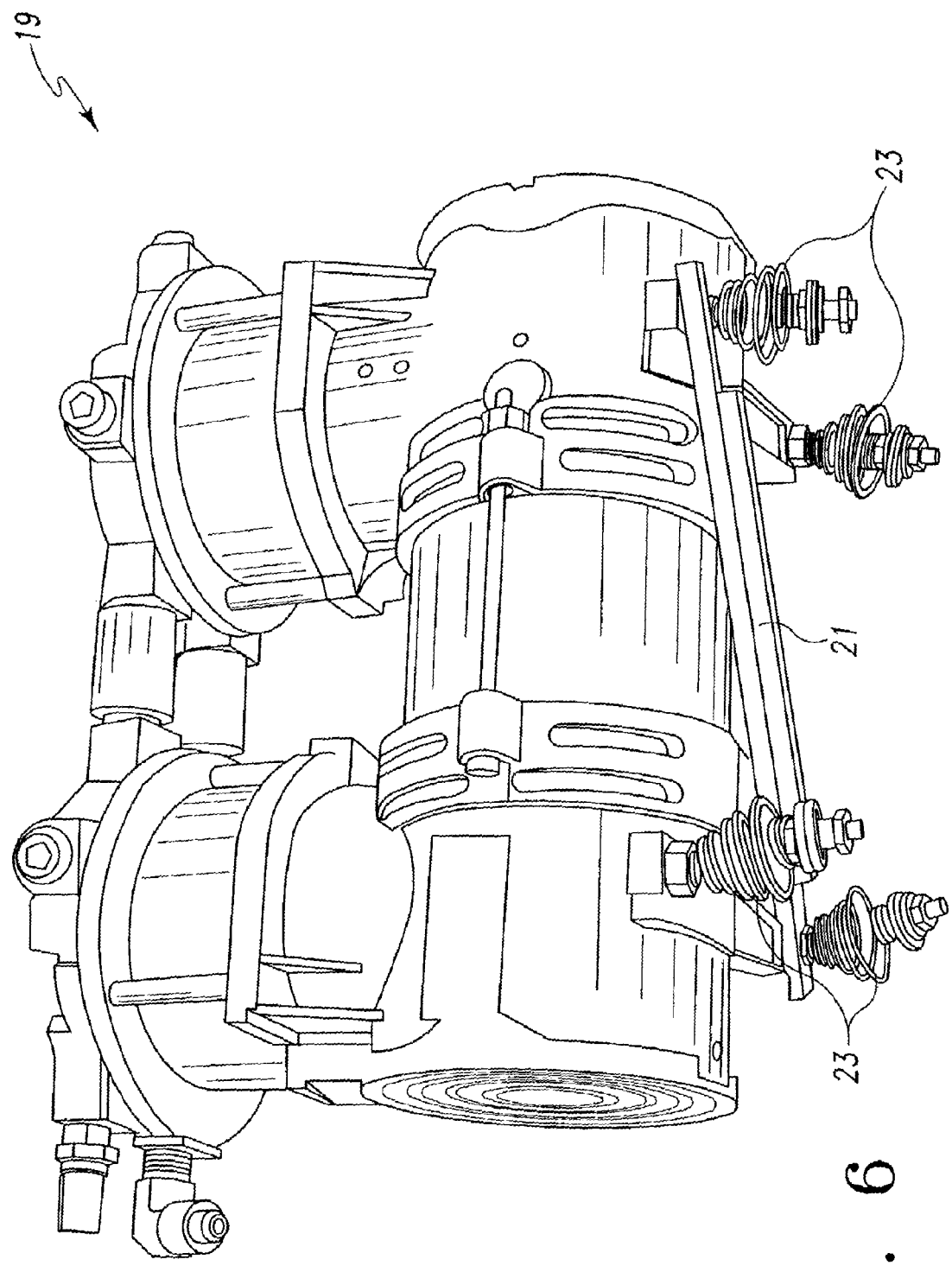
FIG. 6 is a view of a vacuum pump showing the tie-down rail and springs.

A vacuum pump 19 is shown in FIG. 6, the vacuum pump having a tie-down rail 21 and springs 23. FIG. 7 shows the relative placement of vacuum pump 19 and air compressor 11 in the lower portion of console 6. Soundproofing material 37 is also placed in the proximity of vacuum pump 19 and air compressor 11 in order to muffle the sound of air compressor 11 and vacuum pump 19 during operation.

Figure 8:
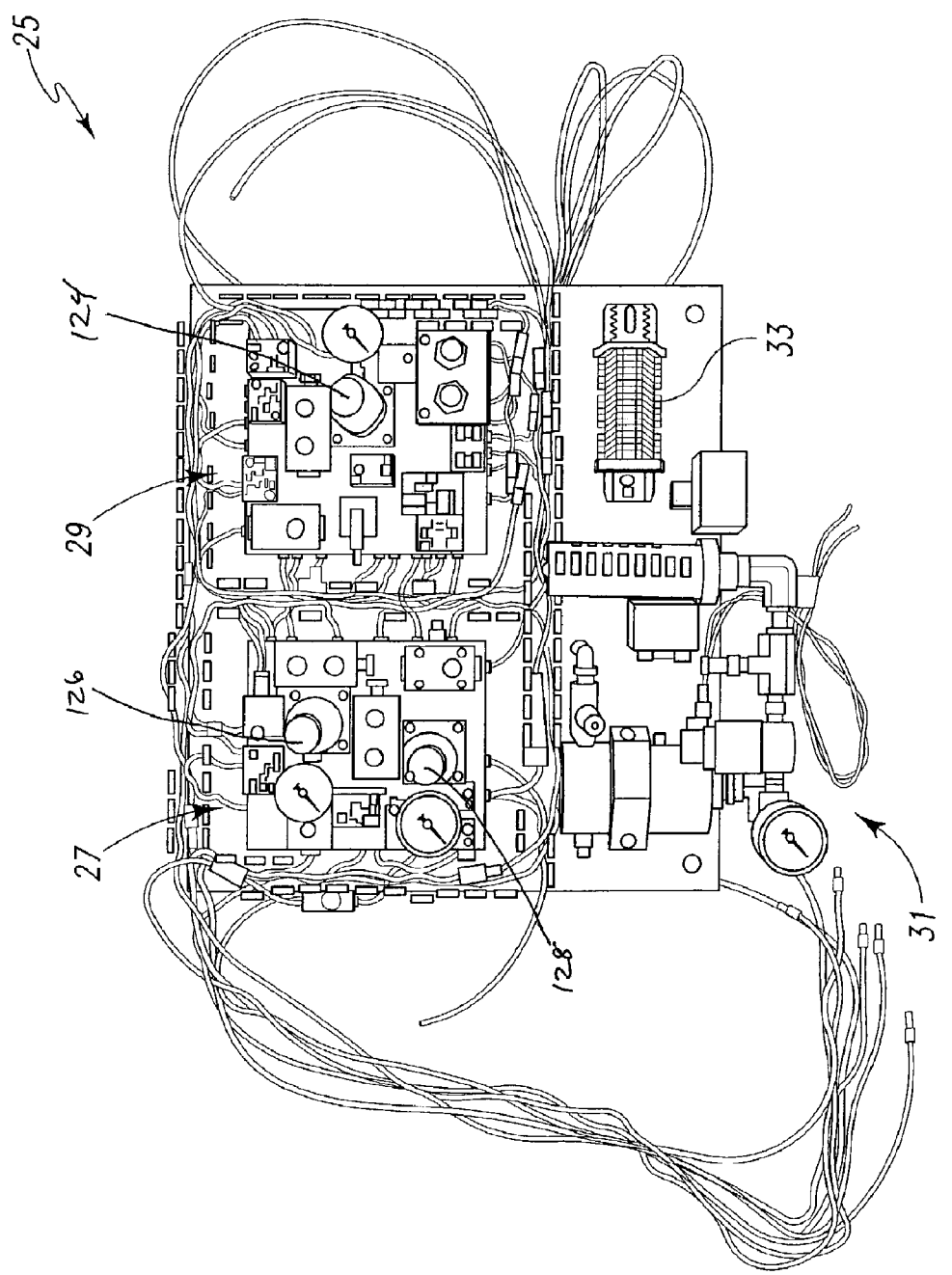
FIG. 8 is a view of a console mounting panel showing manifold subassemblies, a filter subassembly, and a terminal block subassembly mounted on the mounting panel.
Figure 9:
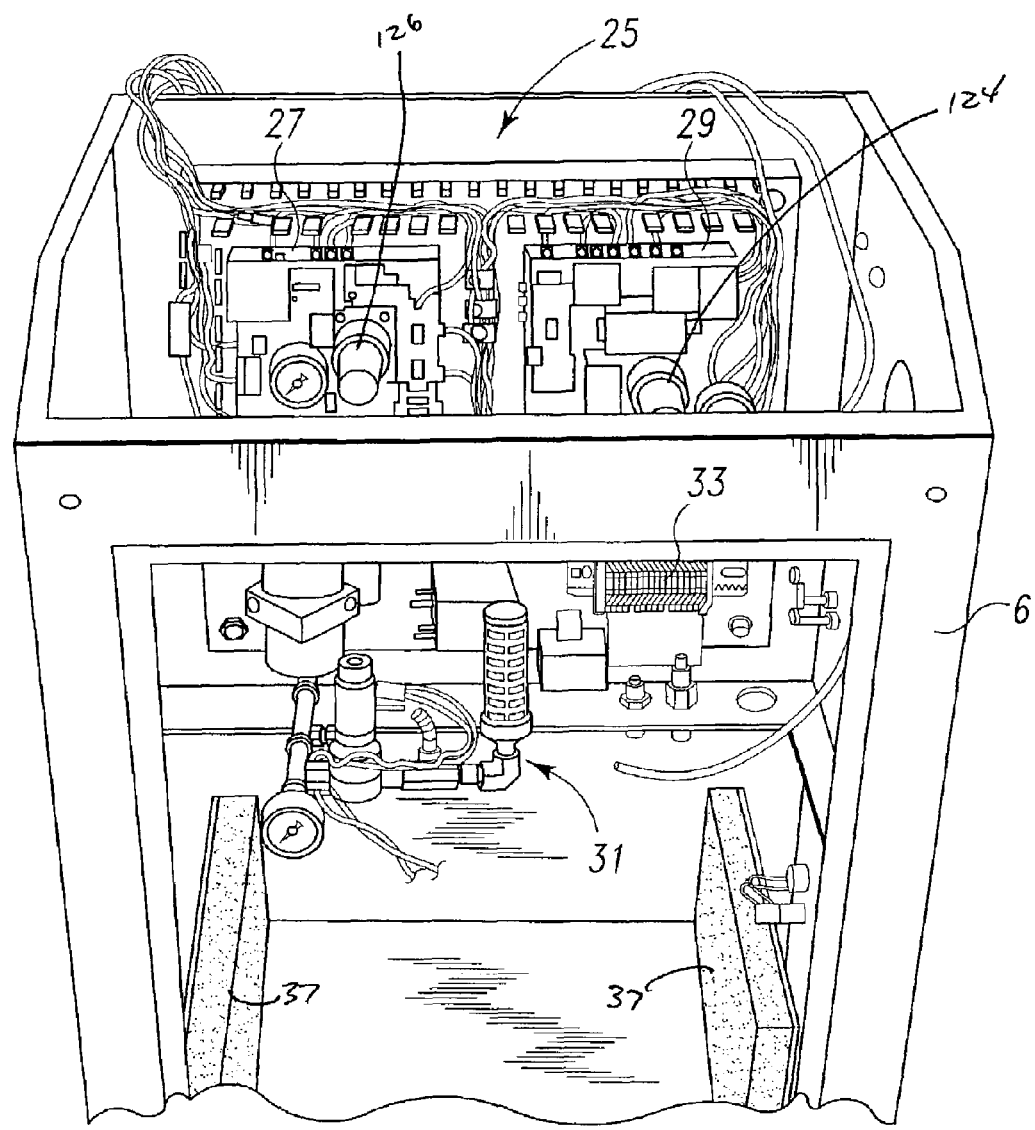
FIG. 9 is a view of the console showing the mounting panel mounted in the console, and showing the cavity in the lower portion which houses the compressor and vacuum.
Figure 10:
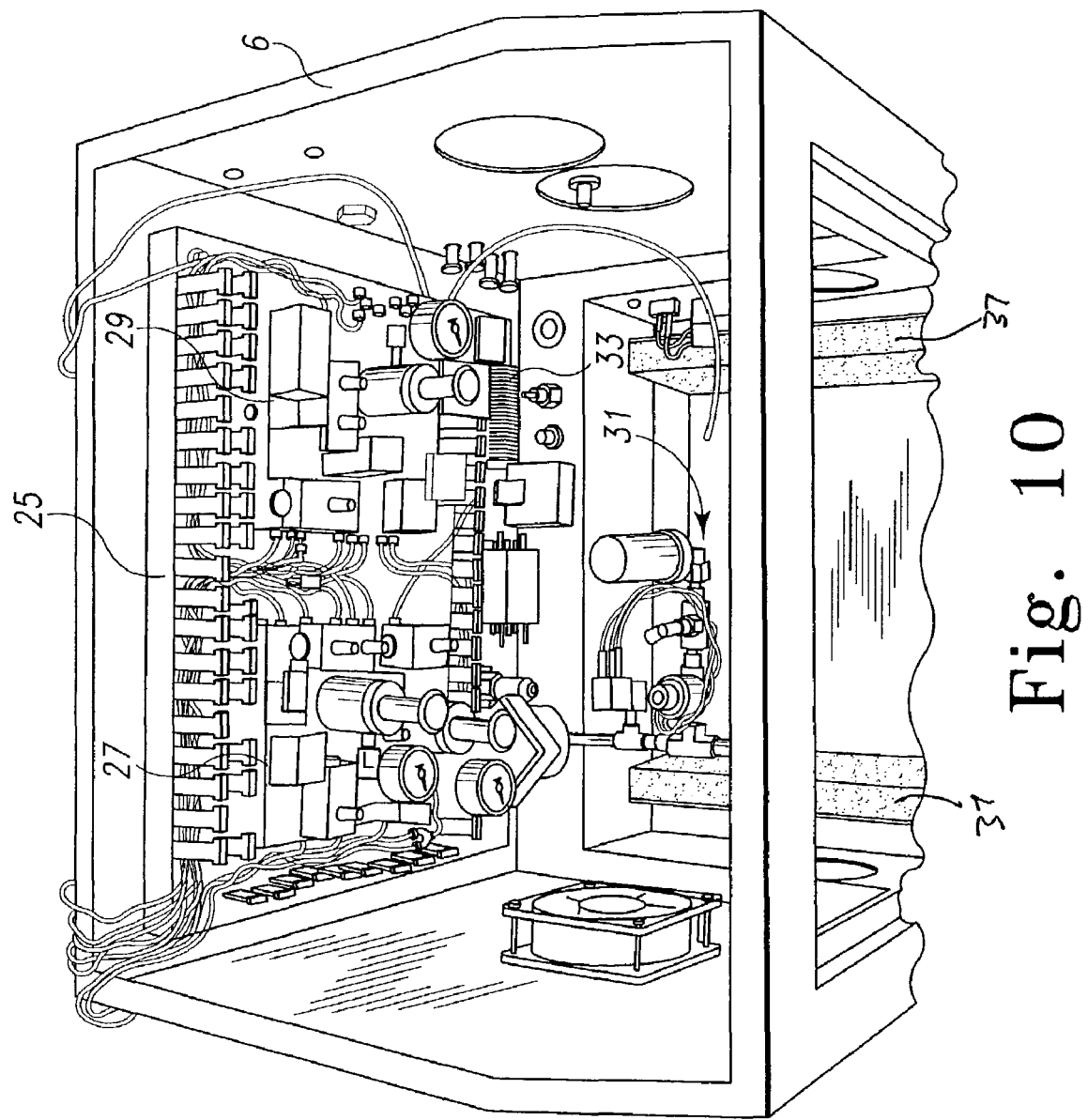
FIG. 10 is a view from the top of the console of FIG. 8.

FIG. 8 is a view of a console mounting panel 25 showing manifold subassemblies 27, 29, an evaporation subassembly 31, and a terminal block subassembly 33 mounted on the mounting panel 25. FIGS. 9 and 10 show the console mounting panel 25 mounted in the console 6. Compressor 11 and vacuum pump 19 are not installed in the illustrative FIGS. 9 and 10.

Figure 11:
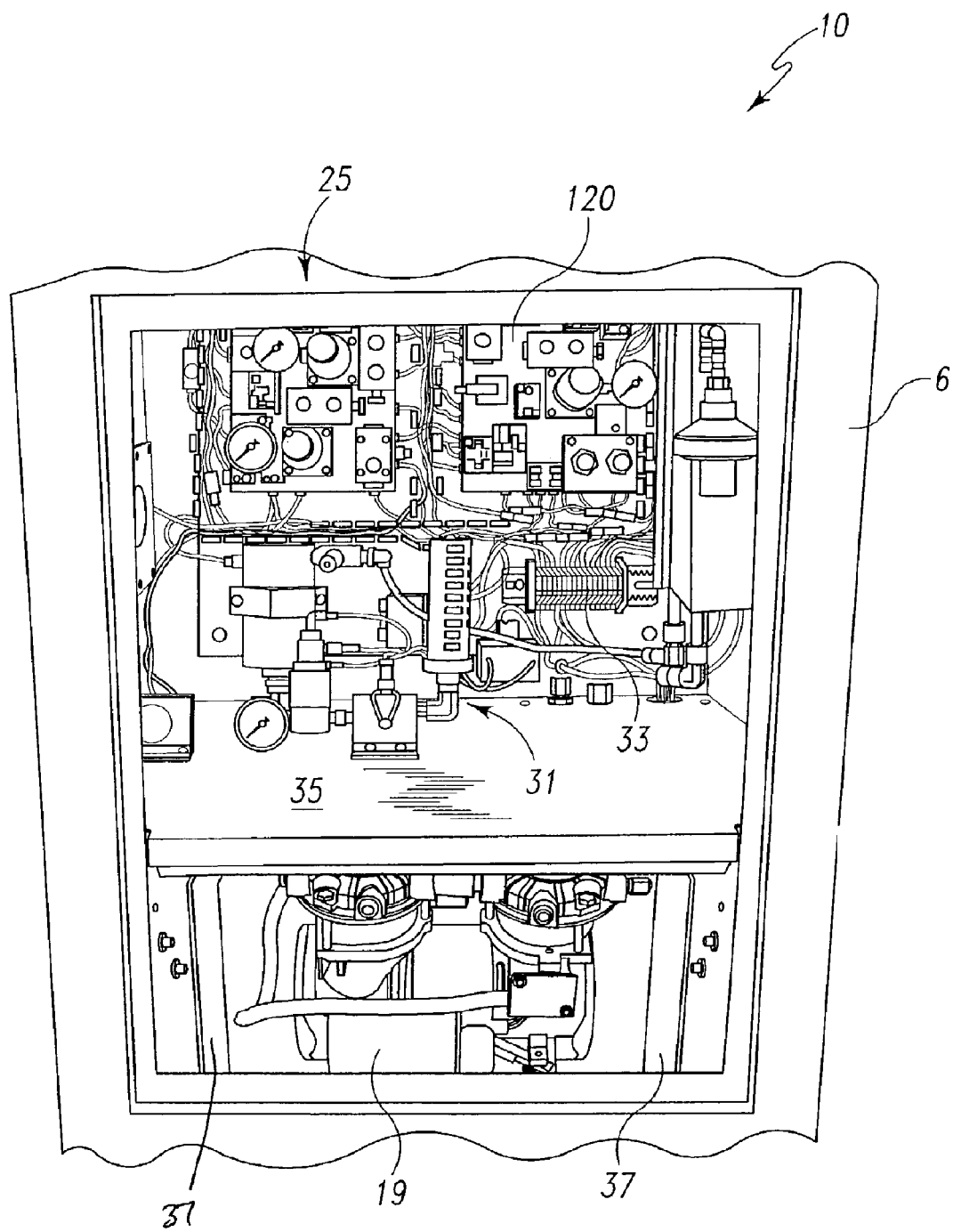
FIG. 11 is a view from the front of the open console similar to that of FIG. 9, showing the compressor and vacuum pump mounted in the lower portion of the console and showing other components of the pneumatic circuit mounted in the upper portion of the console.

Console 6 is shown in FIG. 11 to have compressor 11 and vacuum pump 19 mounted in the console 6 while other components of pneumatic circuit 10 including console mounting panel 25 are mounted in the upper portion of console 6. Shelf 35 is mounted to divide console mounting panel 25 from compressor 11 and vacuum pump 19. As noted above, soundproofing material 37 is positioned to surround compressor 11 and vacuum pump 19.

Figure 12A:
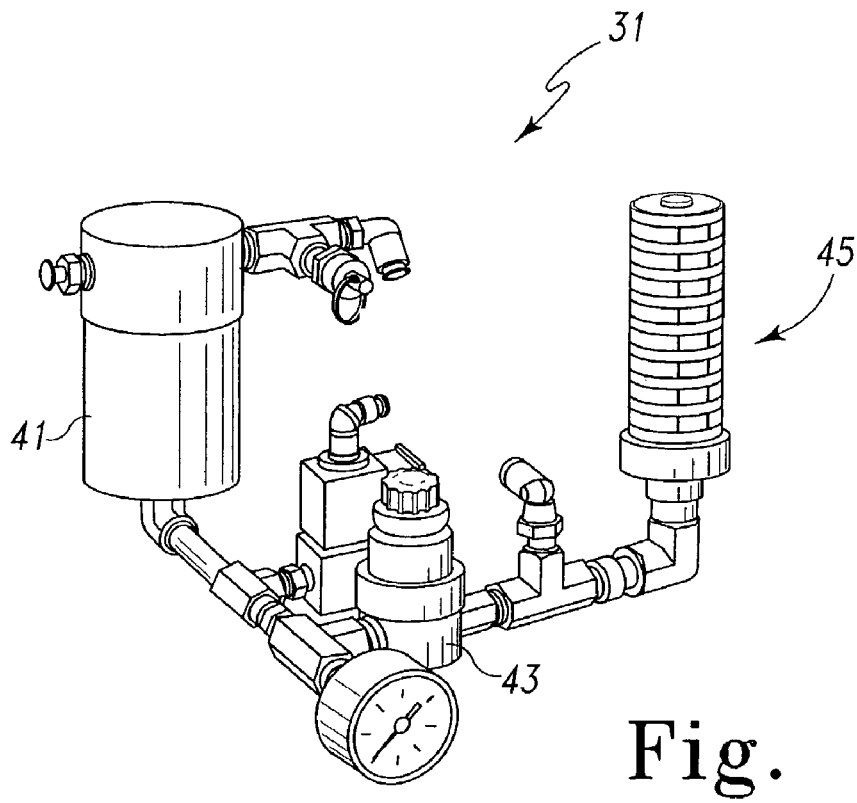
FIGS. 12A-B are views of two embodiments of a water evaporation subassembly.

FIG. 12A shows water evaporation subassembly 31 prior to installation in pneumatic circuit 10. Water evaporation subassembly 31 includes a filter 41, relief regulator 43, and gas-permeable absorber 45. Filter 41 is configured to direct condensation toward gas-permeable absorber 45, which in turn dissipates the condensation into the atmosphere. The schematic representation of water evaporation subassembly 31 can be seen in FIG. 17.

Figure 12B:
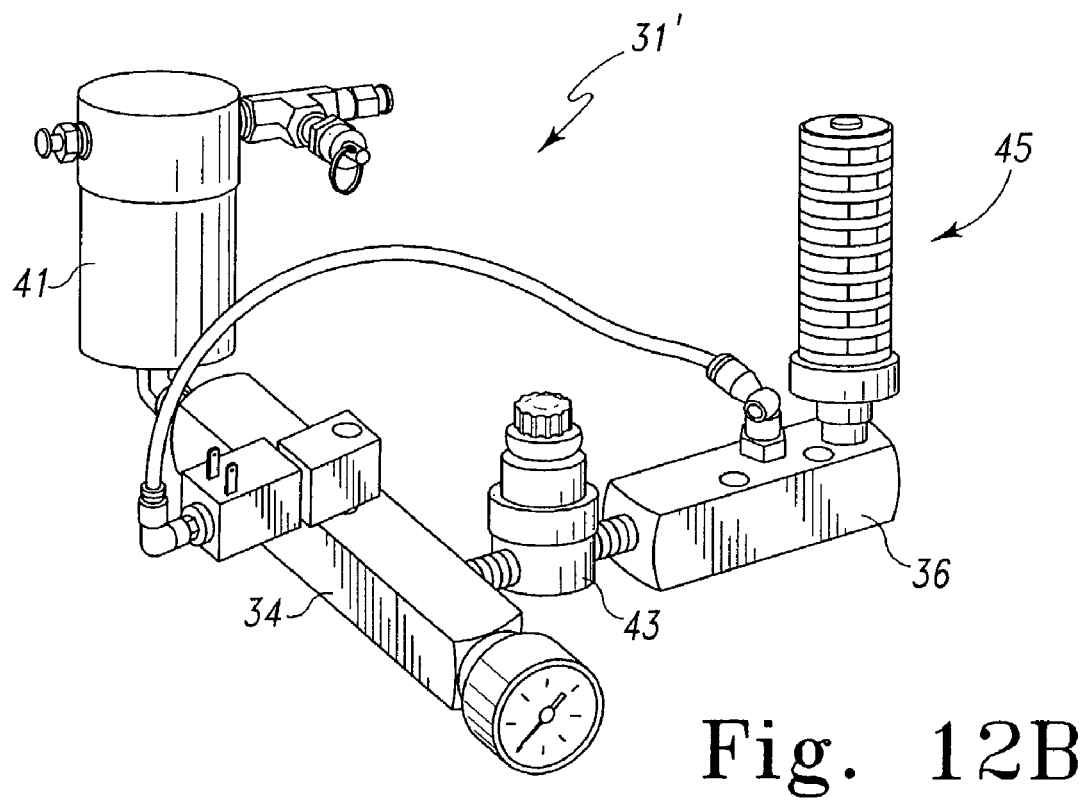

FIG. 12B is an alternative embodiment 31' of the water evaporation subassembly 31 of FIG. 12A. In alternative embodiment 31', conduits and fitting of subassembly 31 are replaced with manifolds 34, 36. Manifolds 34, 36 act as conduits and as fitting receivers for components such as filter 41, relief regulator 43, and gas-permeable absorber 45.

Figure 13B:
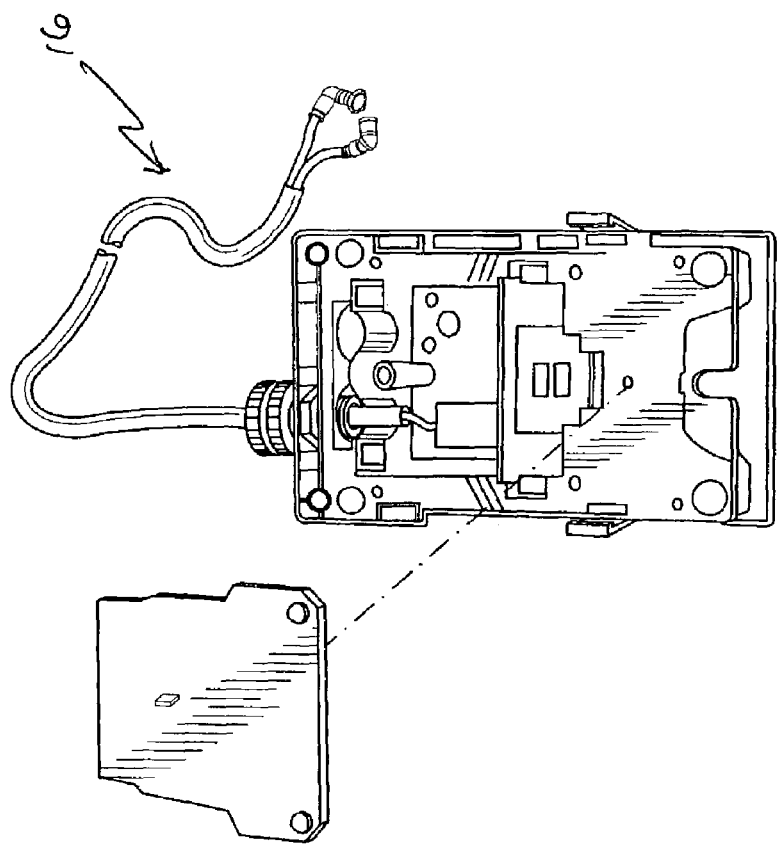
FIGS. 13A-B show, respectively, the foot switch prior to attachment of tubing, and the foot switch partially assembled after the attachment of tubing.
Figure 13A:
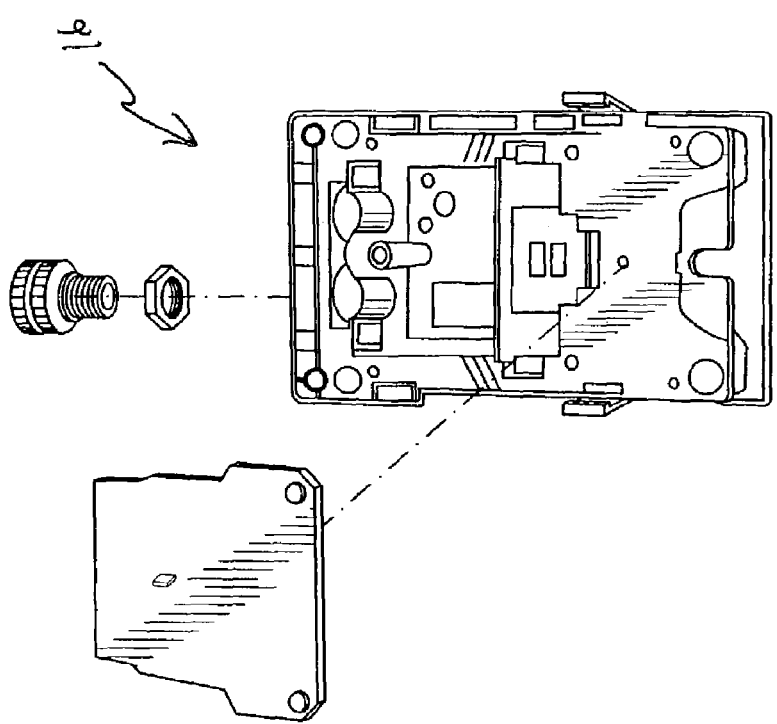

FIGS. 13A and 13B show the assembly of foot switch 16 prior to and after the attachment of tubing. FIG. 14 is a view of the terminal block subassembly 33 prior to installation on the console mounting panel 25, shown in FIG. 8. The terminal block subassembly 33 functions to distribute electrical power to the compressor 11, vacuum pump 19, and dump valves.

Custom designed manifolds 47, 49 can be seen in perspective view in FIGS. 15A-B. Manifolds 47, 49 are configured to route the pneumatic tubing (not shown in FIGS. 15A-B, but viewable in FIG. 8) within the console. Schematics for manifolds 47, 49 can be seen in FIGS. 20B and 21A-D.

Figure 16A:
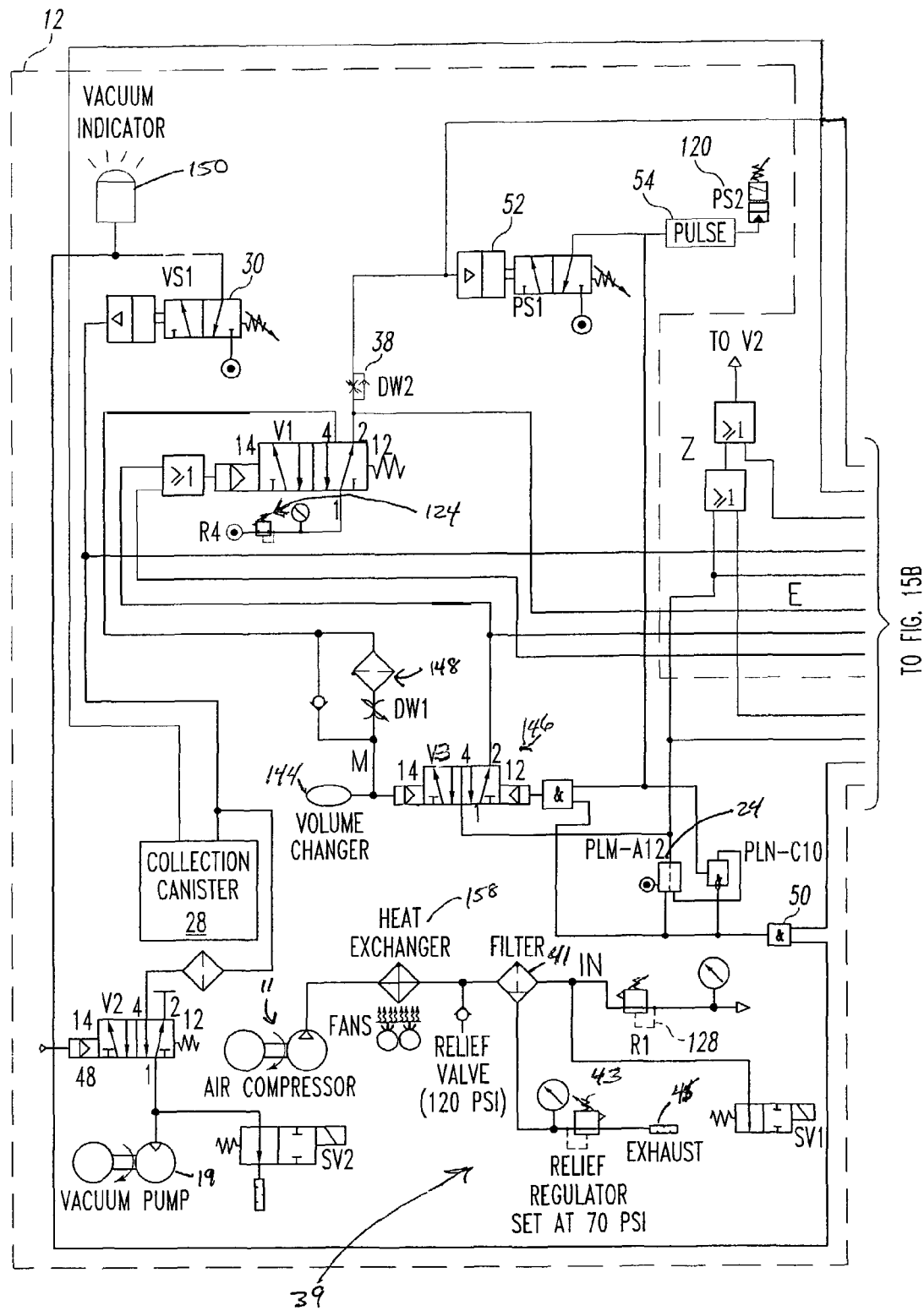
FIGS. 16A-B are schematic representations of the pneumatic circuit elements.
Figure 16B:
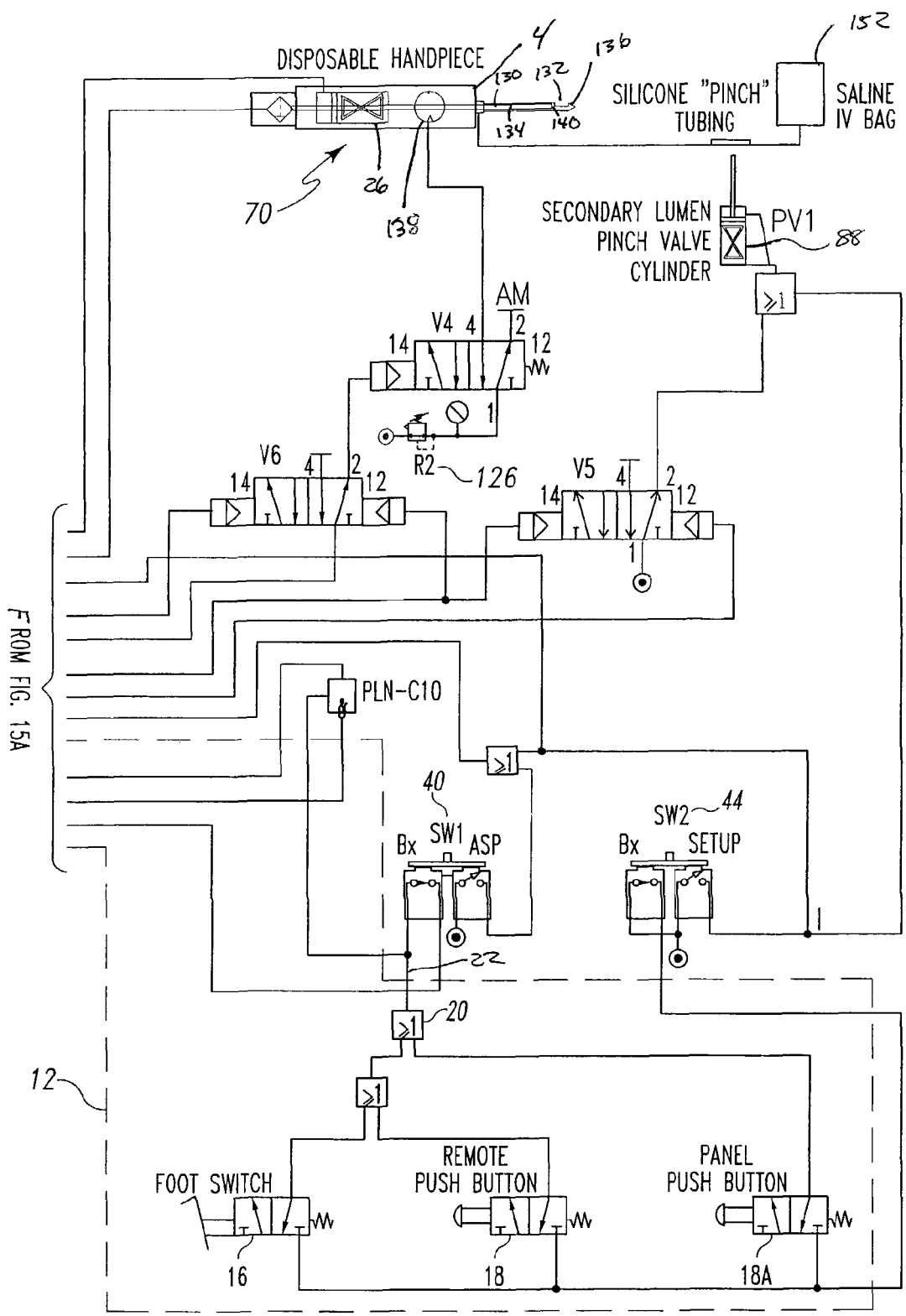

FIGS. 16A-B illustrate the schematic of the illustrative pneumatic circuit 10. Pneumatic circuit 10 includes a first sequence loop 12 (approximated as the elements within the broken lines) and a second sequence loop 14 (outside the broken lines). First sequence loop 12 is initiated with either a foot switch 16, a remote pushbutton 18, or a panel pushbutton 18A. Foot switch 16 is the illustrated embodiment in the drawings, however, any of the above foot switch 16, a remote pushbutton 18, or a panel pushbutton 18A, including combinations thereof, are within the scope of the disclosure.

Sensor 20 (shown in FIG. 16B) senses pressurization and permits passage of pressurized gas through path 22 when foot switch 16, pushbutton 18, or pushbutton 18A is actuated, or any combination thereof. The pressurized gas shifts the vacuum valve 48 (FIG. 16A), creating vacuum in collection canister 28. Vacuum sensor 30 passes a signal to the vacuum indicator 150 when the vacuum level reaches 20" Hg vacuum. Pressurized signals from components 30, 22 pass through the "and" gate 50 (FIG. 16A) and latch relay 24, which in turn signals cutter cylinder 26 to retract to a non-extended position. When cutter cylinder 26 is retracted into the non-extended position, pressurized gas is delivered to medical device 70, illustratively to operate pneumatic motor 138. However, it should be understood that pressurized gas may be utilized for any number of functions in a medical device, and is not restricted to the illustrative functions shown in hand wand 4.

A saline supply 152 (FIG. 16B) is also illustratively provided to medical device 70, the saline supply 152 fostering the flow of biological material removed by the medical device 70 to collection canister 28. Pinch valve 72, which includes pneumatically actuated stopper 88 (FIG. 16B), controls the flow of saline supply 152 in a manner described further herein.

Collection canister 28 collects biological material from the medical device 70 during the medical procedure using vacuum pressure. In addition to the biological material being collected, saline is collected in this manner. If the vacuum pressure fails, such failure is sensed by vacuum switch 30, and the cycle stops. Otherwise, pressurized gas continues to be delivered for a period of time determined by timing circuit 148.

Timing circuit 148 incorporates a restricted orifice that fills volume chamber 144 with gas and eventually signals valve 146 to turn on the pressurized gas to medical device 70. Pressurized gas causes cutter cylinder 26 to advance at a rate controlled by timing circuit 38 until it reaches the extended position (also the position held during insertion of the cannula of the illustrative medical device, described above). Such pressurized gas continues to build up in medical device 70 until pressure sensor 52 senses a predetermined gas pressure in cutter cylinder 26 and illustratively trips at approximately 24 psi, indicating the end of the stroke. At such a point, signaling device 54 causes a momentary audible signal, and also latch relay 24 resets, turning off device 70. If signal 22 is still present, the relay 24 will not reset and the process will automatically repeat. If the process repeats the audible tone has a shorter duration than if it resets.

It is also possible that cutter cylinder 26 does not fully advance to the extended position before pressure sensor 52 trips. In such an instance, cutter cylinder 26 may encounter difficulties cutting through the mass 142, and pressure will build up in cutter cylinder 26 even though the end of the stroke has not been reached. When the cylinder pressure reaches the predetermined amount of 24 psi, sensor 52 trips, regardless of the position of cutter cylinder 26 (and the attached cutter 134).

Setup switch 44 (FIG. 16B), which is controlled by knob 154 on control panel 9 (FIG. 1) allows an operator to load the saline tube into the pinch valve 72 and primes the medical device by actuating, in parallel, the retraction of cutter cylinder 26, the opening of saline pinch valve 72, and the opening of vacuum valve 48. During this setup mode, signals from 22 are ignored, thereby inhibiting a cycle start condition. Aspiration switch 40 (FIG. 16B), which is controlled by knob 156 on control panel 9 (FIG. 1) inhibits a cycle start condition and causes cylinder 26 to retract, if a signal delivered via path 22 is present the vacuum valve 48 shifts creating vacuum in the canister and the medical device.

Referring to FIGS. 16A-B, pneumatic circuit 10 operates in substantially the following fashion. Air compressor 11 is turned on and creates air pressure and flow. The compression process creates heat and condenses the humidity in the air. At such a point, condensed water is in gaseous state. The hot moist air is then passed through a fan-driven air-to-air heat exchanger 158 cooling the air and changing the water to a liquid state. The cooled air is then passed into a coalescing filter 41 where the water is captured in the filter media and drips into the bottom of the filter bowl. The filtered air then continues out to feed the control circuit.

The compressor runs continuously. If pressure is sensed by the relief regulator of greater than the set point of 70 psi, it will continuously vent the excess pressure. If the system is on and not in cycle, 99% of the compressor flow rate will vent out of the relief regulator. While the system is cycling the medical device, approximately 40% of the system capability will continuously flow through the relief regulator.

The water that is collected in the bottom of the filter bowl is dissipated with water evaporation subassembly 39. Water passes from the filter 41 through the relief regulator 43 and into the base of the permeable exhaust member 45. The exhaust member 45 acts as a wick, drawing the fluid up the media. The flow rate through the exhaust member 45 and the large "wick" surface area cause the liquid water to evaporate into a gas state. The flow rate through the enclosure caused by the heat exchanger fans removes the water vapor from the cabinet, thus eliminating the need to collect water and drain it from the system. Illustratively, a filter "muffler" is used as a permeable exhaust member 45, the muffler being available from Allied Witan Company, of Cleveland, Ohio, as part number F02.

The pneumatic circuit components are mounted to custom aluminum manifolds 47, 49 minimizing the use of fittings and keeping the system compact. The components are "sub-base" style versions of the component allowing for ease of replacement. Each component that needs adjusted is bench tested and set to the specified level using certified fixtures. Diagrammatic representations of the manifolds can be seen in FIGS. 21 A-D.

Console 6 is designed to isolate the noise and heat created by compressor 11 and vacuum pump 19. Design specifications for console 6 can be seen in FIGS. 19A-D. Shelf 35 divides the cabinet into two sections. The lower section contains the spring-mounted pumps 11, 19, soundproofing material 37, and fans to isolate vibration, heat, and noise, as can be seen in FIG. 7.

Figure 22A:
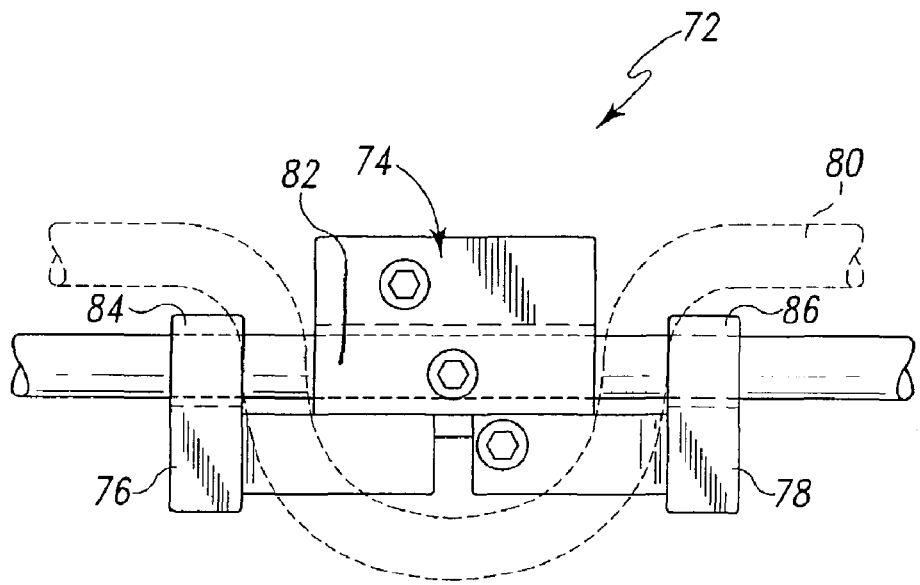
FIG. 22A shows a top view of a pinch valve configured to control the flow of saline.
Figure 22B:
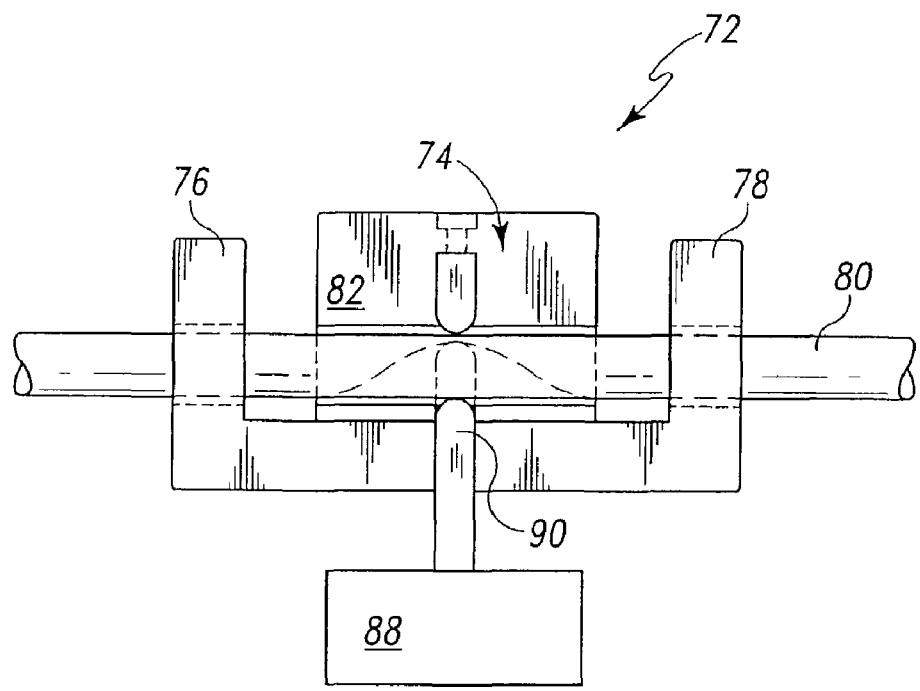
FIG. 22B is a front elevation view of the pinch valve shown in FIG. 22A, showing the tube positioned in the pinch valve, and showing the movement of the plunger between a flow position and a non-flow position.
Figure 24A:
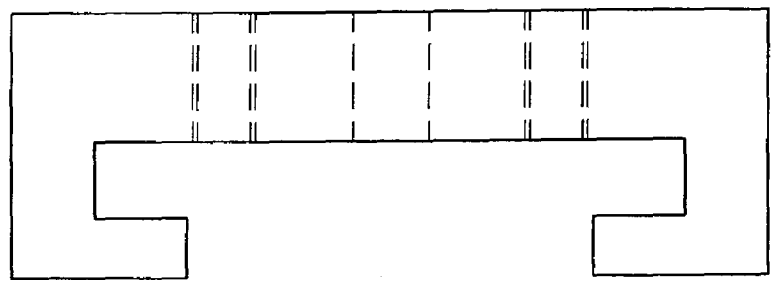
FIGS. 24A-B show a top view and a front elevation view, respectively, of a canister bracket.
Figure 24B:
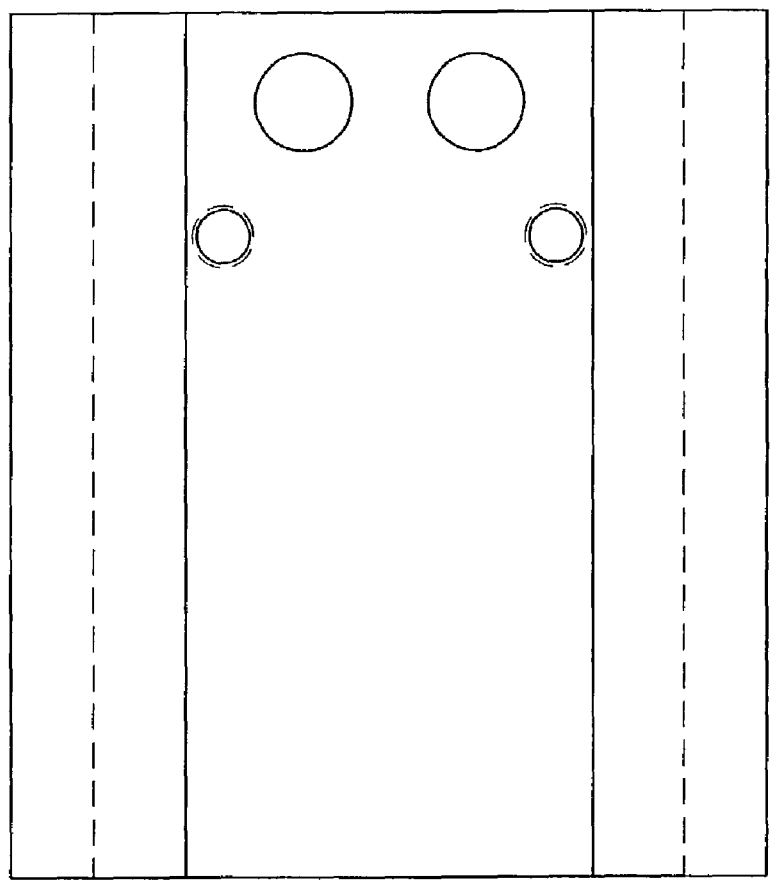
Figure 25B:
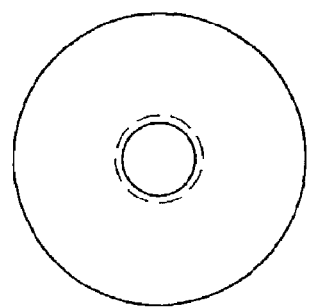
FIGS. 25A-D show front and side views of a pair of hose wrap pins.
Figure 25D:
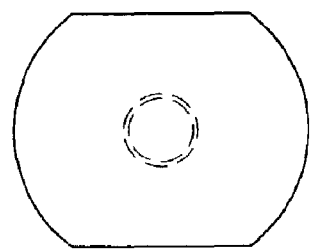
Figure 25A:
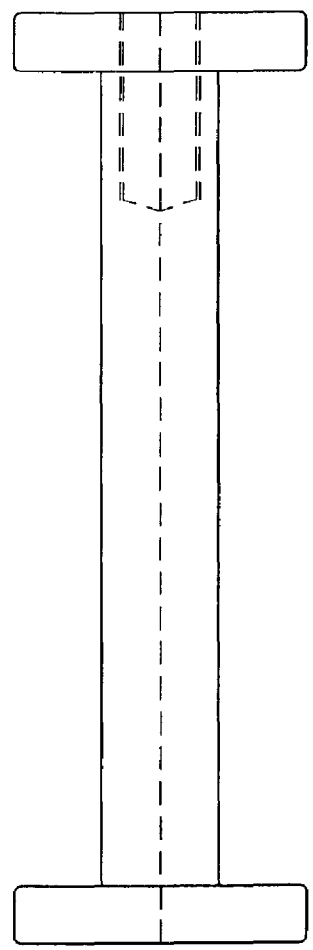
Figure 25C:
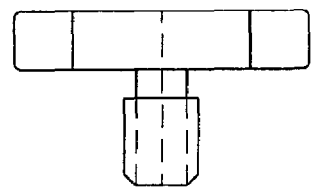

As shown in various views in FIGS. 22A-B, pinch valve 72 includes a retainer comprised of a central catch 74 and opposing catches 76, 78. See also a view of pinch valve 72 in FIG. 1. Silicone tubing 80 is bent into a configuration as shown in broken lines, and pushed between central catch 74 and opposing catches 76, 78. When pulled taut, silicone tubing 80 assumes a substantially straight configuration and is disposed under cantilevered portion 82 of central catch 74, and cantilevered portions 84, 86 of opposing catches 76, 78 respectively, as shown in FIG. 22A. Such a configuration secures the silicone tubing 80 and prevents accidental removal of silicone tubing 80 from pinch valve 72.

Pneumatically actuated stopper 88, shown diagrammatically in FIG. 22B, moves a piston 90 between a stopped position (shown in broken lines) and a flow position. The default position is the stopped position, stopping the flow of fluid through the silicone tubing 80.

Figure 26A:
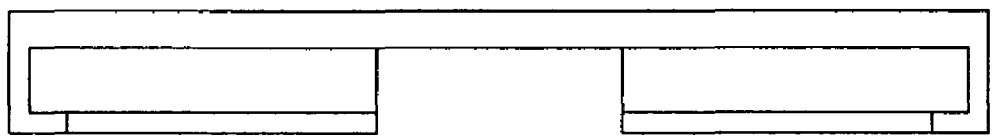
FIGS. 26A-B show a foot switch holder.
Figure 26B:
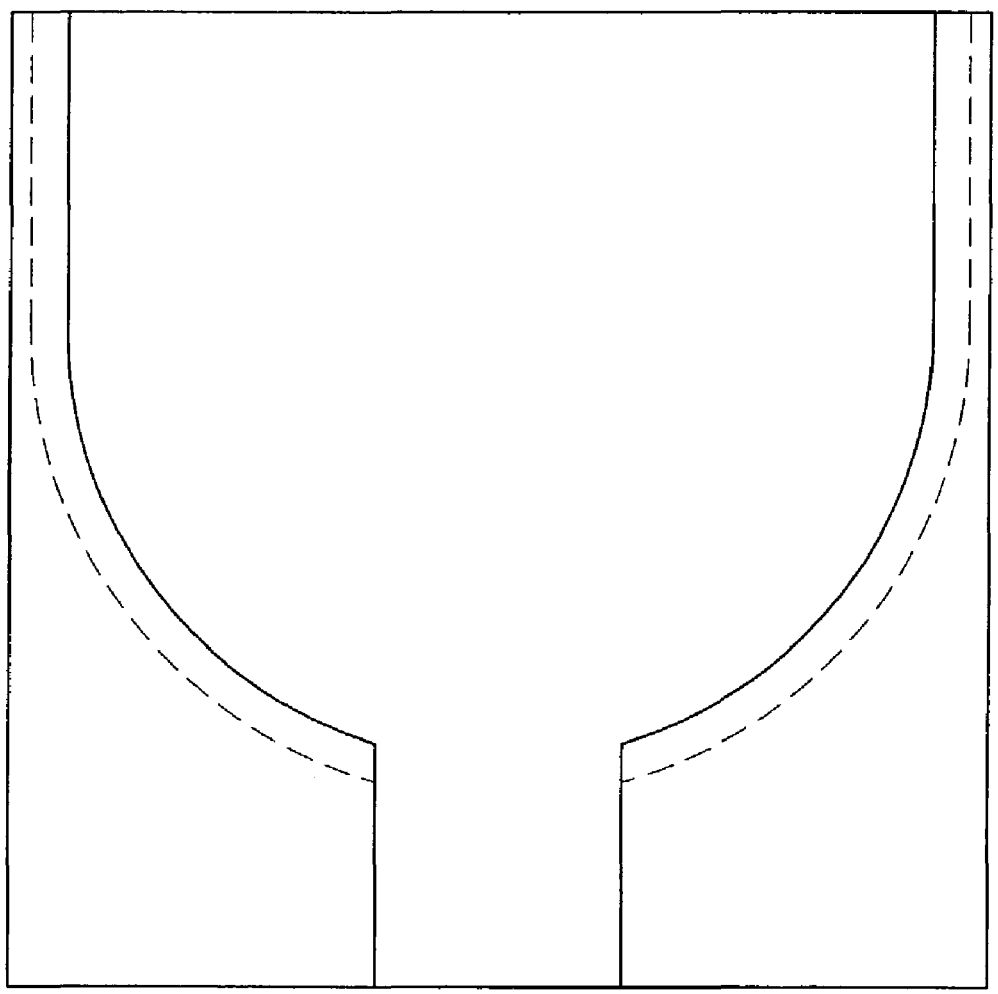
Figure 27:
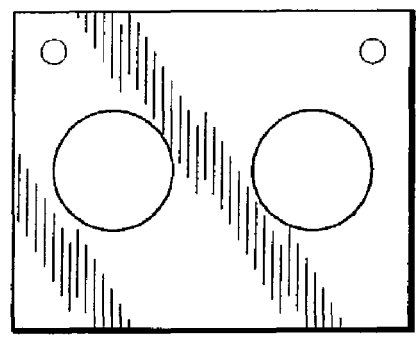
FIG. 27 shows a valve bracket.
Figure 28A:
FIGS. 28A-B show an embodiment of tie-down rails.
Figure 28B:

FIGS. 25A-D show a pair of hose wrap pins that is used to wrap the foot switch tube set and the power cord when the system is not in use. FIGS. 26A-B show a foot switch holder. FIG. 27 shows a valve bracket. And FIGS. 28A-B show an embodiment of tie-down rails.

Figure 29:
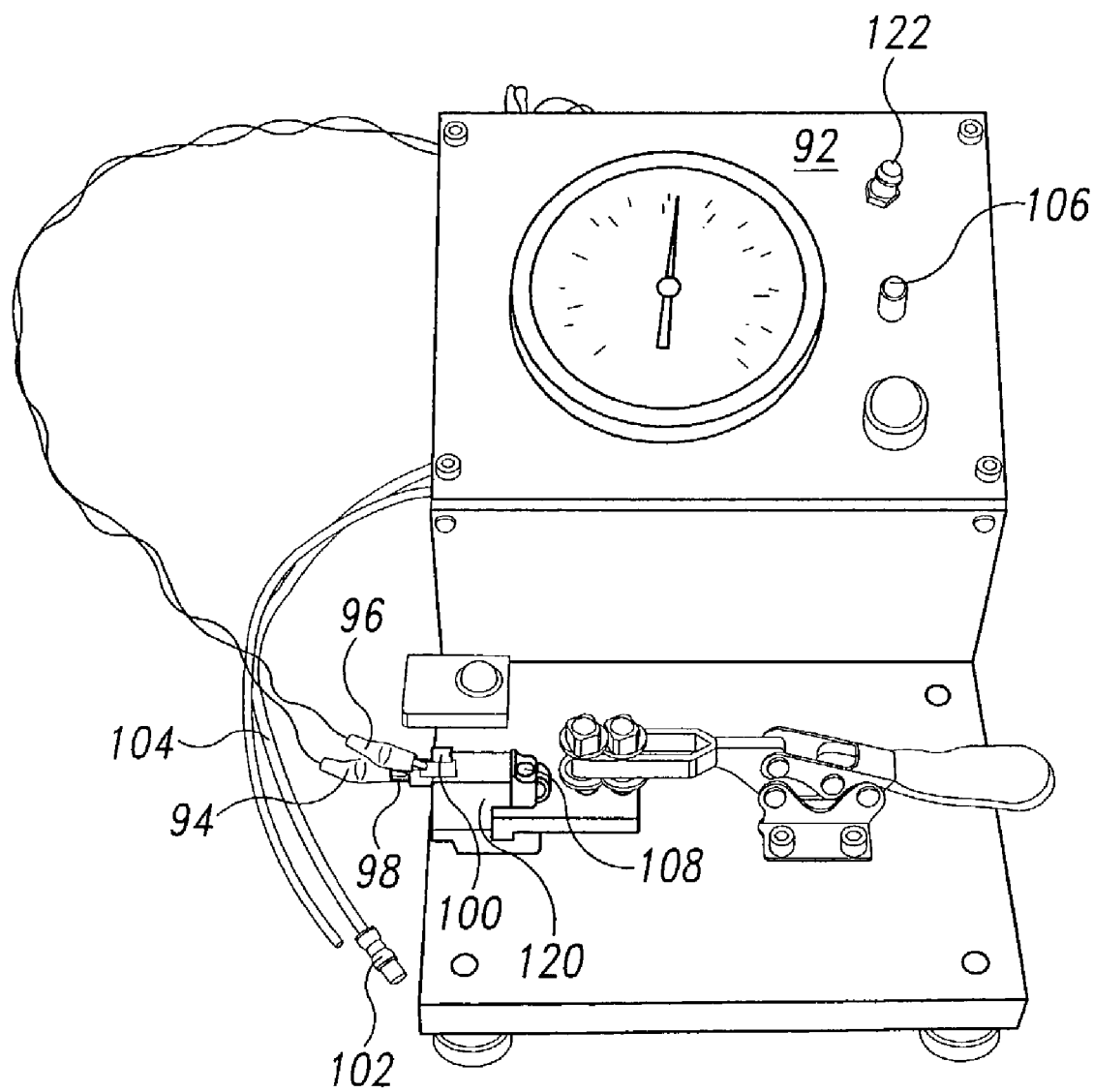
FIGS. 29-33 show the test equipment used in testing certain elements in the pneumatic circuit in various stages of the test.

The test module 92 for testing Airtrol electric pressure switch 120 (as shown in FIGS. 11 and 16A), model number F-4200-60-MM, can be seen in FIGS. 29-33. The switch 120 is placed on test module 92 and clamped in place, as seen in FIG. 29. A red jumper 94 is connected to the normally open (N.O.) terminal 98 of switch 120. Black jumper 96 is connected to COM terminal 100. A plugged union fitting 102 is connected to an end of natural colored tube 104. With an air supply to test module 92 turned on, 2-position detented button 122 is pulled out and pressure observed. It is further observed when green indicator light 106 turns on. If green indicator light 106 does not turn on at 20 psi+/−0.5 psi, then button 122 should be pushed back in and adjustments made to switch 120, and testing done again. After the proper target pressure is obtained, a green dot sticker 108 is placed over the adjustment screw. Pneumatic vacuum switch VP-701-30-MM is tested in a similar fashion, with a targeted setting of 20" Hg vacuum.

Figure 30:
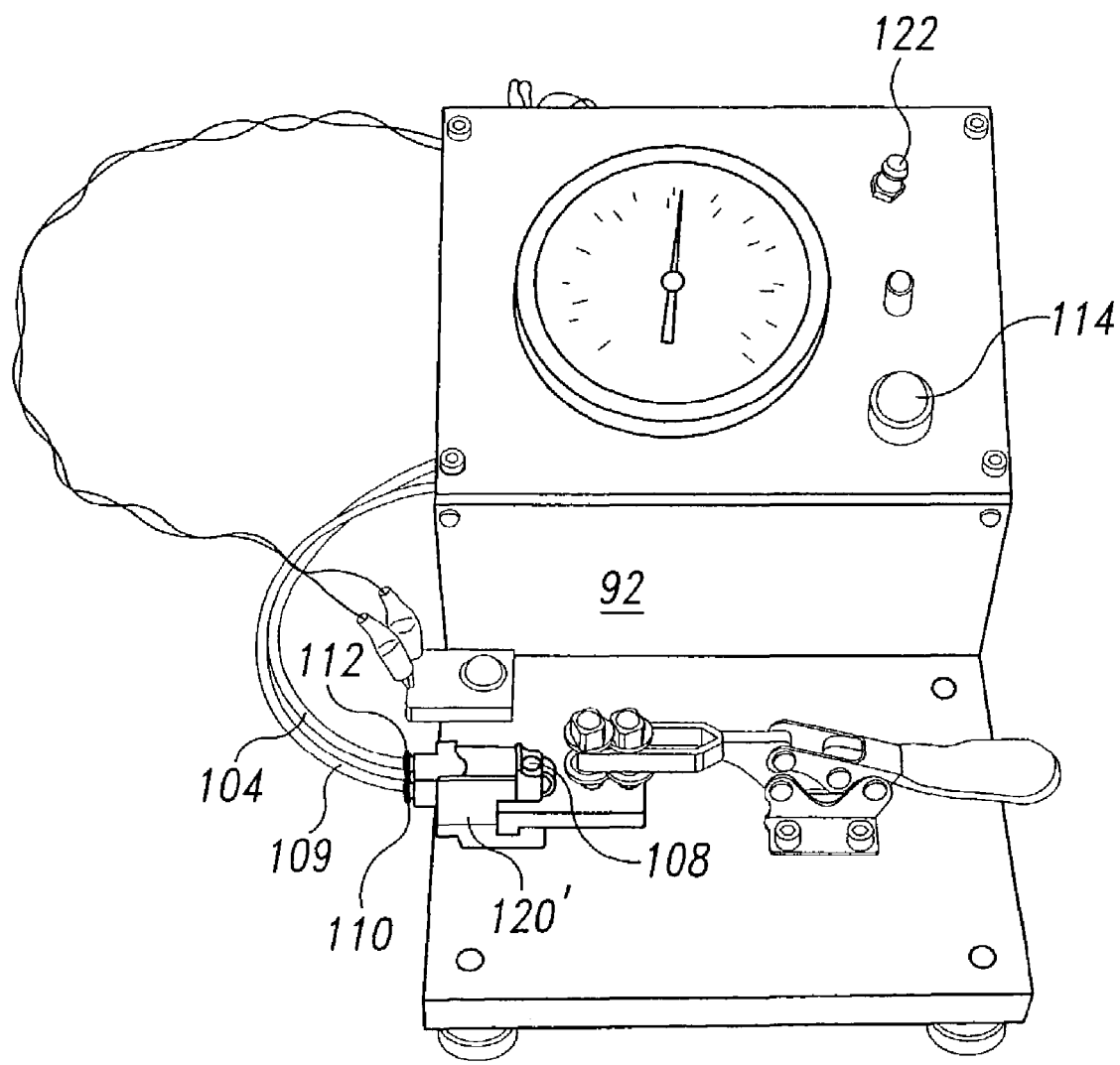
Figure 31:
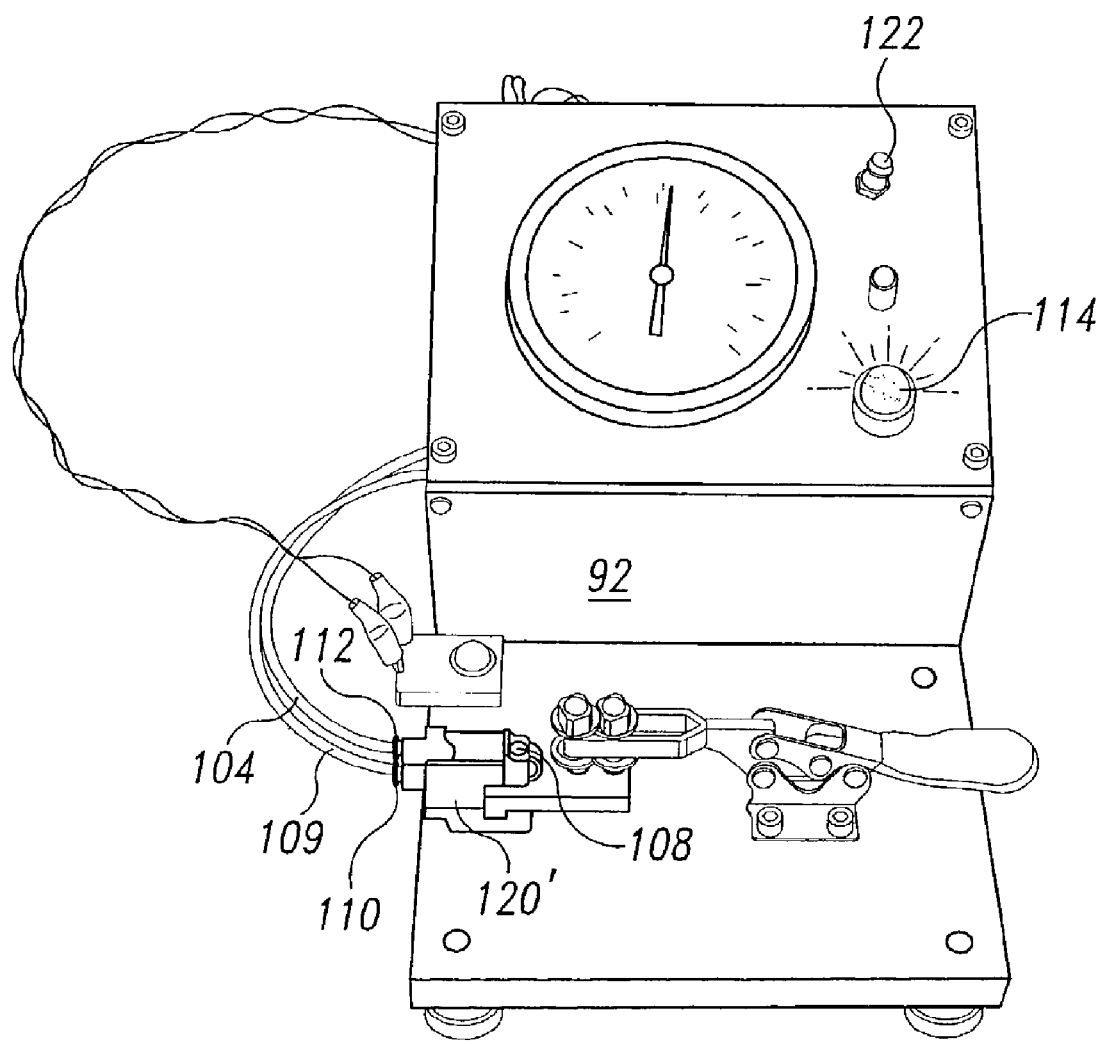

Another test procedure for test module 92 is shown in FIGS. 30 and 31. In such a procedure, Airtrol pneumatic pressure switch 120' (model number PP-701-30-MM) is tested. Red tube 109 is connected to output port 110. Natural tube 104 is connected to input port 112. With an air supply to test module 92 turned on, button 122 is pulled out and pressure at which large green light 114 comes on is observed. If large green light 114 does not turn on at 24 psi+/−0.5 psi, then button 122 should be pushed back in and adjustments made to switch 120', and testing done again. After the proper target pressure is obtained, a green dot sticker 108 is placed over the adjustment screw.

Figure 32:
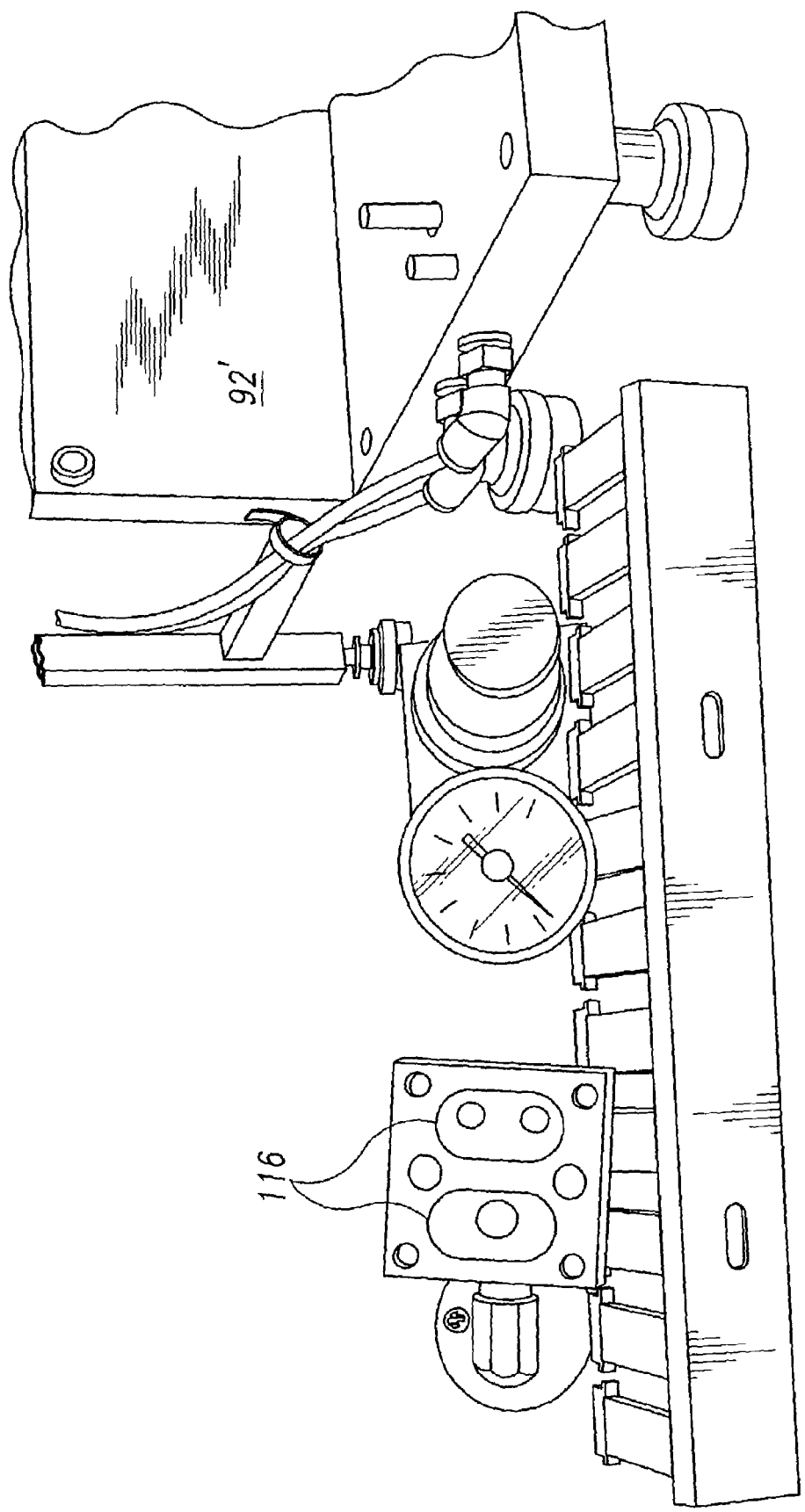
Figure 33:
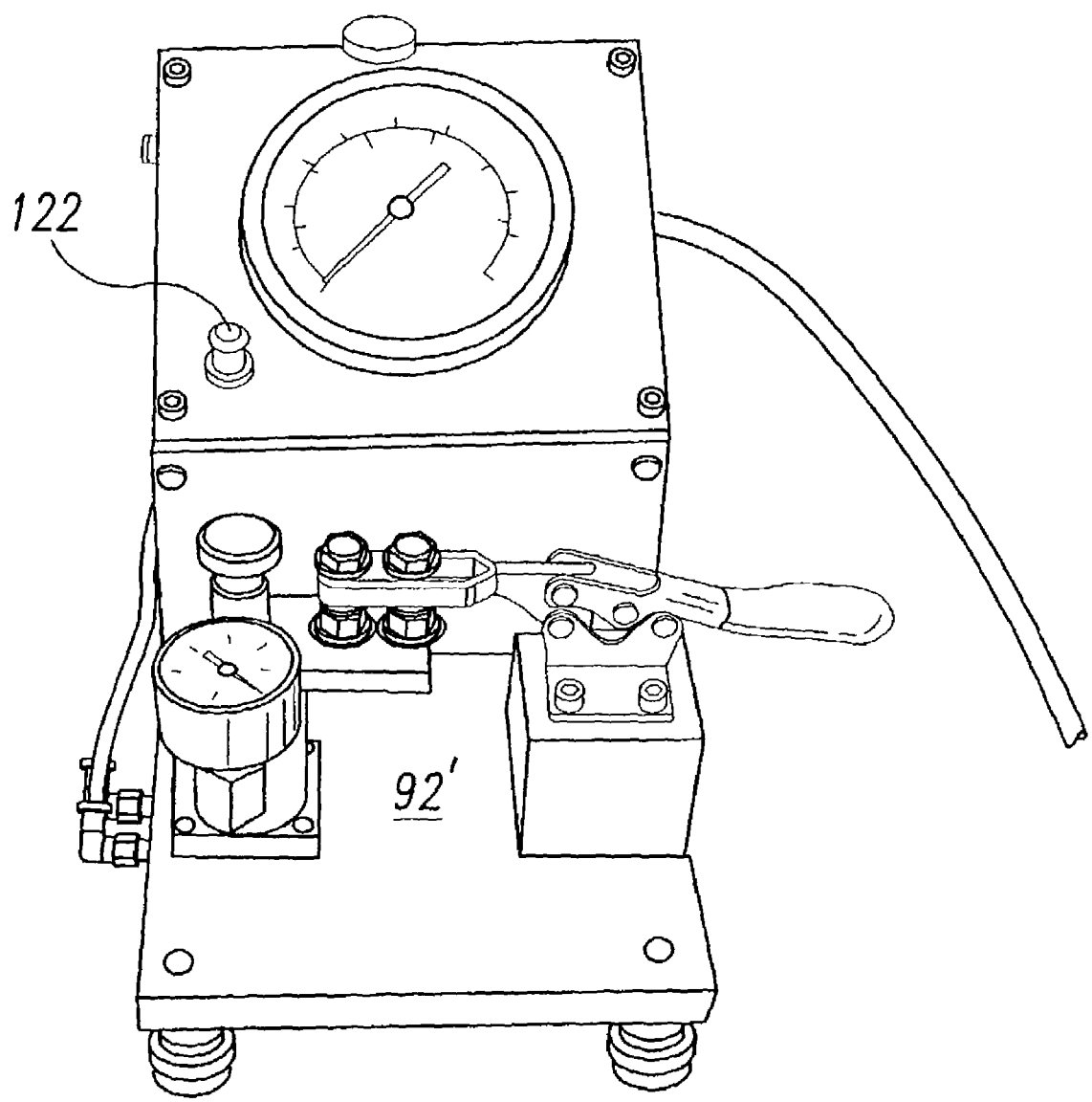

Yet another test module 92' for testing various regulators is shown in FIGS. 32 and 33. This test module 92' is illustratively used for the cutter cylinder regulator 124 (model R4, R01-10 w/60 psi gauge), the air motor regulator 126 (model R2, R01-12 w/60 psi gauge), and the main regulator 128 (model R1, R01-12 w/160 psi gauge). The regulators are illustrated schematically in FIGS. 16A-B, and on diagrammatic views of the manifolds in FIGS. 20B and 21A-B. During testing, the tested regulator 124, 126, 128 should be set for the appropriate target pressure (60 psi, 60 psi, and 160 psi, respectively). Next, two O-rings 116 (seen in FIG. 32) should be installed in the bottom of the tested regulator. The regulator 124, 126, 128 is then placed on the test module 92' aligning the locating pin and locating hole found on the test module and regulator. Regulator 124, 126, 128 is then clamped in place.

Target pressures during testing of regulators 124, 126, 128 varies depending on the regulator. Model R4 is targeted for 30 psi, rising. Model R2 is targeted for 40 psi, rising. Model R1 is targeted for 60 psi, rising. Once pressure is dialed in to the appropriate target, the regulator nut is tightened to prevent knob movement and a permanent marker is used to mark the cannula position of the regulator gauge. Finally, a green dot is placed in the center of the gauge face.

Illustrative parts used in the production of the above-described embodiment can be found in FIGS. 34A-C. It should be understood, however, that other parts and constructions are within the scope of the disclosure.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

A plurality of advantages arises from the various features of the present disclosure. It will be noted that alternative embodiments of various components of the disclosure may not include all of the features described yet still benefit from at least some of the advantages of such features. Those of ordinary skill in the art may readily devise their own implementations of a pneumatic circuit that incorporate one or more of the features of the present disclosure and fall within the spirit and scope of the disclosure.

What is claimed is:

1. A pneumatic circuit comprising:
    a cabinet;
    a compressor housed inside the cabinet, the compressor being configured to compress a gas;
    a biopsy device in pneumatic communication with the compressor, the biopsy device capable of being actuated by the compressed gas from the compressor;
    an exit port in pneumatic communication with the compressor and positioned inside the cabinet, wherein moisture from the pneumatic circuit passes through the exit port; and
    a fan configured to produce a flow of air inside the cabinet, the flow of air facilitating the evaporation of the moisture from the cabinet.

2. The pneumatic circuit of claim 1, further comprising a media positioned to receive moisture from the exit port.

3. The pneumatic circuit of claim 2, wherein the media is a permeable material configured to absorb moisture from the pneumatic circuit.

4. The pneumatic circuit of claim 2, wherein the media is absorbent.

5. The pneumatic circuit of claim 2, wherein the media is an absorber.

6. The pneumatic circuit of claim 2, wherein the media and pneumatic circuit are housed inside the cabinet, and the media facilitates the evaporation of liquid within the cabinet.

7. The pneumatic circuit of claim 1, wherein the biopsy device comprises a pneumatic motor for creating rotational motion of a cutter blade about an axis.

8. The pneumatic circuit of claim 1, wherein the fan is positioned on an exterior wall of the cabinet.

9. A method of removing moisture from a cabinet housing a pneumatic circuit, wherein the pneumatic circuit is configured to operate a medical device, the method comprising:
    using a compressor to compress air;
    intermittently operating the medical device while the compressor is compressing air;
    releasing moisture from the pneumatic circuit through an exit port; and
    using a fan to direct a flow of air within the cabinet.

10. The method of claim 9, further comprising the step of using a media to temporarily hold the moisture.

11. The method of claim 10, further comprising the step of directing the flow of air over the media.

12. The method of claim 10, further comprising the step of evaporating moisture from the media.

13. The method of claim 9, wherein the medical device is a biopsy device.

14. The method of claim 9, further comprising the step of dissipating heat from the pneumatic circuit.

15. The method of claim 9, wherein the exit port is configured to release compressed air when the medical device is not in operation.

16. A pneumatic circuit comprising:
    a compressor for compressing a gas;
    a biopsy device in pneumatic communication with the compressor, the biopsy device capable of being actuated by the compressed gas from the compressor;
    a media configured to absorb moisture from pneumatic circuit; and
    a fan configured to direct a flow of air over the media.

17. The pneumatic circuit of claim 16, wherein the media is a permeable material configured to absorb moisture from the pneumatic circuit.

18. The pneumatic circuit of claim 17, wherein the media is absorbent.

19. The pneumatic circuit of claim 16, wherein the fan facilitates the evaporation of moisture from the media.

20. The pneumatic circuit of claim 16, wherein the media and pneumatic circuit are housed in a cabinet, and the fan facilitates the evaporation of liquid within the cabinet.

* * * * *